United States Patent
Meisberger et al.

(10) Patent No.: US 9,927,336 B2
(45) Date of Patent: Mar. 27, 2018

(54) APPARATUS AND METHODS FOR LOW TEMPERATURE SMALL ANGLE X-RAY SCATTERING

(71) Applicant: CORNELL UNIVERSITY, Ithaca, NY (US)

(72) Inventors: Stephen P. Meisberger, Ithaca, NY (US); Matthew A. Warkentin, Ithaca, NY (US); Jesse B. Hopkins, Ithaca, NY (US); Andrea M. Katz, Ithaca, NY (US); Lois Pollack, Ithaca, NY (US); Robert E. Thorne, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 452 days.

(21) Appl. No.: 14/405,253

(22) PCT Filed: Jun. 4, 2013

(86) PCT No.: PCT/US2013/044088
§ 371 (c)(1),
(2) Date: Dec. 3, 2014

(87) PCT Pub. No.: WO2013/184665
PCT Pub. Date: Dec. 12, 2013

(65) Prior Publication Data
US 2015/0233804 A1    Aug. 20, 2015

Related U.S. Application Data

(60) Provisional application No. 61/655,210, filed on Jun. 4, 2012.

(51) Int. Cl.
*G01N 23/00*    (2006.01)
*G01N 1/42*    (2006.01)
*G01N 23/201*    (2018.01)

(52) U.S. Cl.
CPC ............. *G01N 1/42* (2013.01); *G01N 23/201* (2013.01)

(58) Field of Classification Search
CPC ............................... G01N 1/42; G01N 23/201
See application file for complete search history.

(56) References Cited

U.S. PATENT DOCUMENTS 5,059,025 A * 10/1991 Ando ................... G01N 21/253
356/244
6,441,617 B2    8/2002 Marek
(Continued)

FOREIGN PATENT DOCUMENTS

WO    2005098463 A2    10/2005

OTHER PUBLICATIONS

International Search Report for Application No. PCT/US2013/044088, International Filing dated Jun. 4, 2013 pp. 1-14.

*Primary Examiner* — Dani Fox
(74) *Attorney, Agent, or Firm* — Bond, Schoeneck & King, PLLC; William Greener; Frederick Price

(57) ABSTRACT

Apparatus and methods for performing small angle X-ray scattering (SAXS) at low (cryogenic) temperatures for determining the structure of and changes in the structure of proteins, DNA, RNA, and other biological molecules and biomolecular assemblies and structures. A cryogenic, small angle X-ray scattering (SAXS) application sample holder, includes a sample cell including a base portion and at least two parallel walls disposed on the base, wherein the sample cell has a liquid volume capacity defined by the walls and the base portion of 0.001 to 10 microliters. A method for performing cryogenic SAXS on a sample includes the steps of providing a sample biomolecule solution containing an aqueous buffer, a biomolecule, and a cryoprotectant agent, wherein the cryoprotectant agent comprises up to 60% (w/w) of the biomolecule solution, and other known com- (Continued)

ponents as necessary to solubilize and stabilize the biomolecule, in a sample holder of claim 1, cryogenically cooling the sample solution in the sample holder at a rate equal to or greater than 100 K/sec without ice formation, and examining the cooled sample using small angle X-ray scattering by passing a beam of X-rays through the sample.

17 Claims, 16 Drawing Sheets

(56) References Cited

U.S. PATENT DOCUMENTS

| | | | |
|---|---|---|---|
| 6,562,127 B1 * | 5/2003 | Kud | C30B 33/06 |
| | | | 117/915 |
| 2006/0130493 A1 | 6/2006 | Strobel | |
| 2009/0133410 A1 | 5/2009 | Thorne et al. | |
| 2012/0007599 A1 | 1/2012 | Prestegard | |
| 2013/0259201 A1 * | 10/2013 | Amenitsch | G01N 21/51 |
| | | | 378/86 |

* cited by examiner

Fig. 2
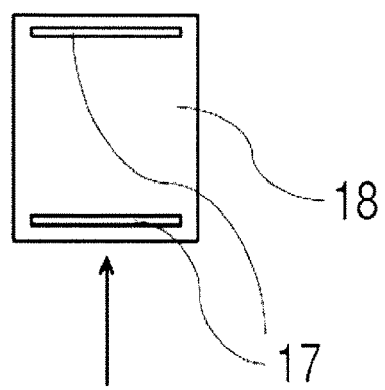
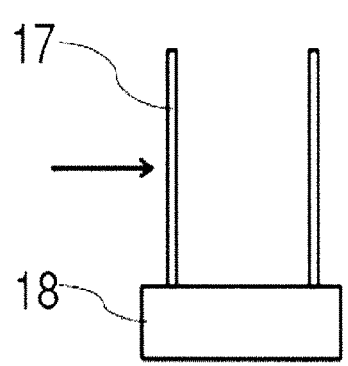
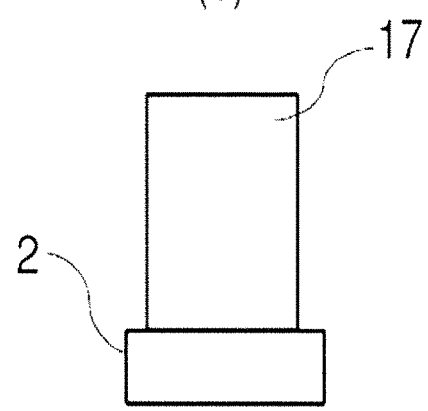

Fig. 5
(a)
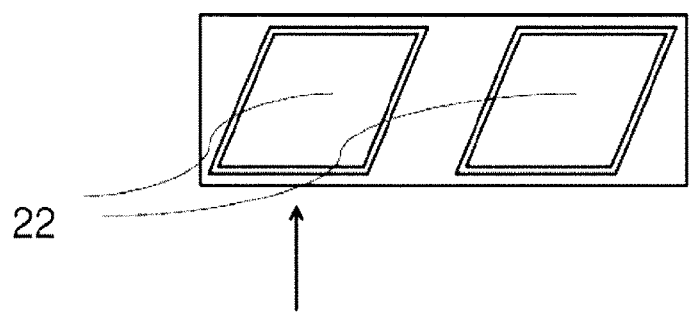
22
(b)
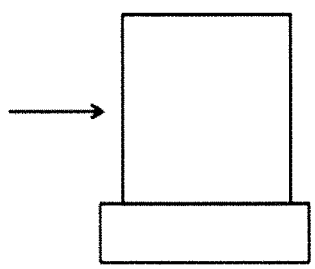
(c)
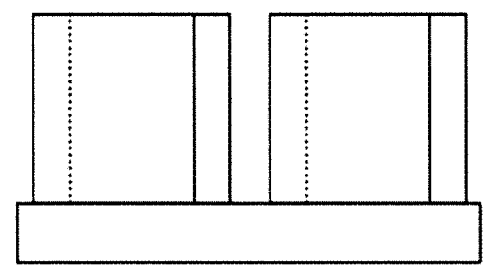

Fig. 7
(a) 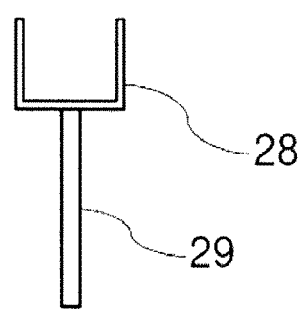
(b) 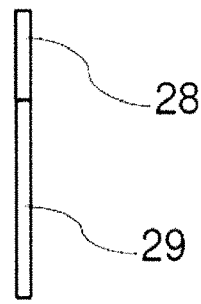
(c) 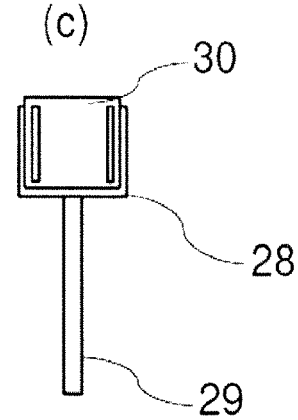
(d) 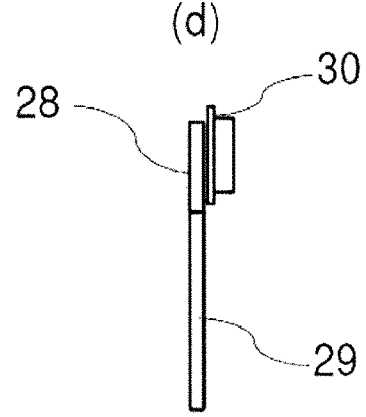

Fig. 9
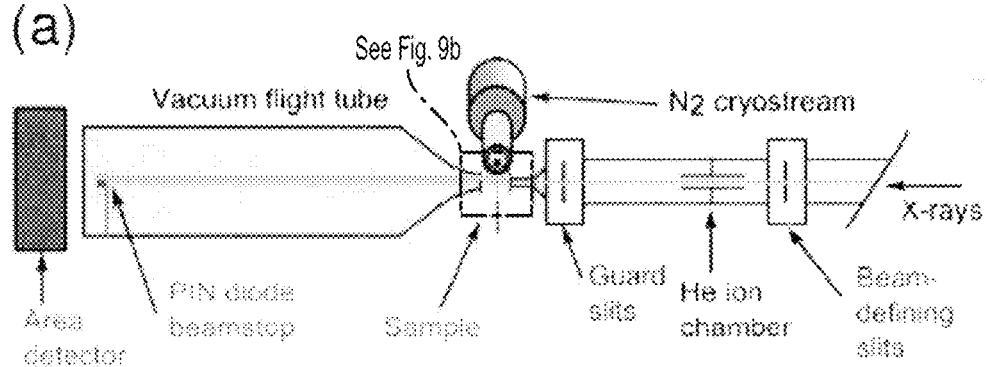
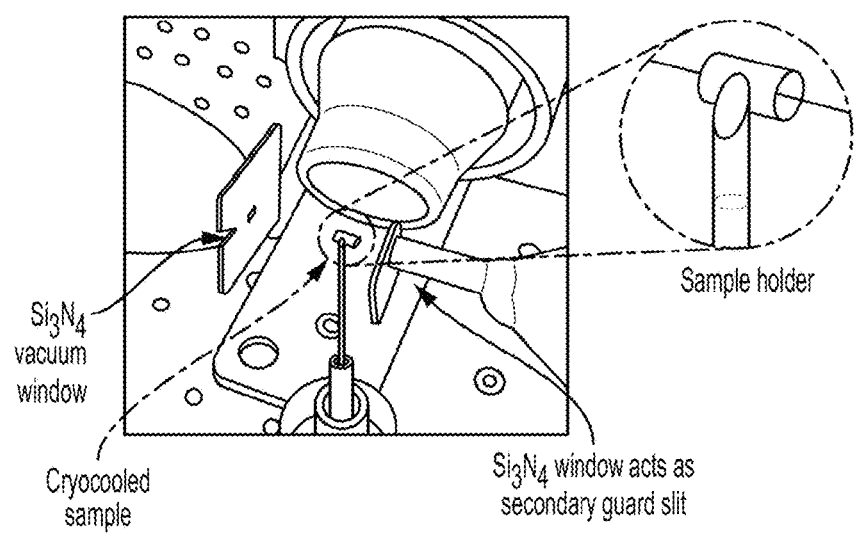

Fig. 10
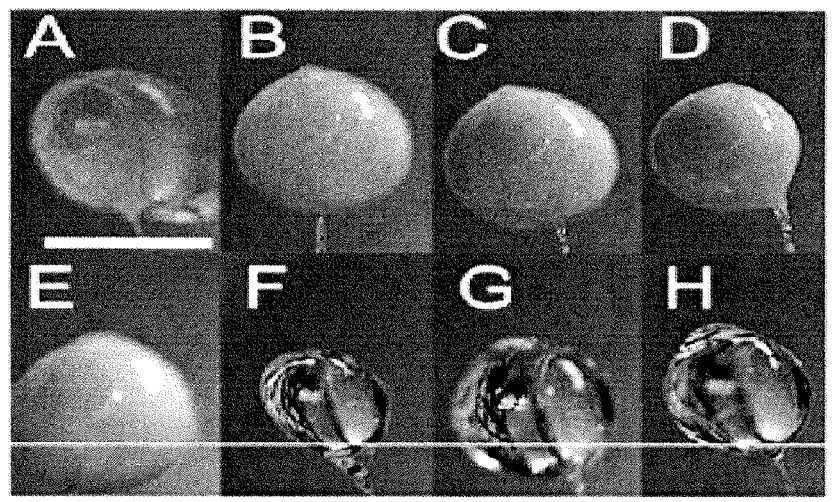
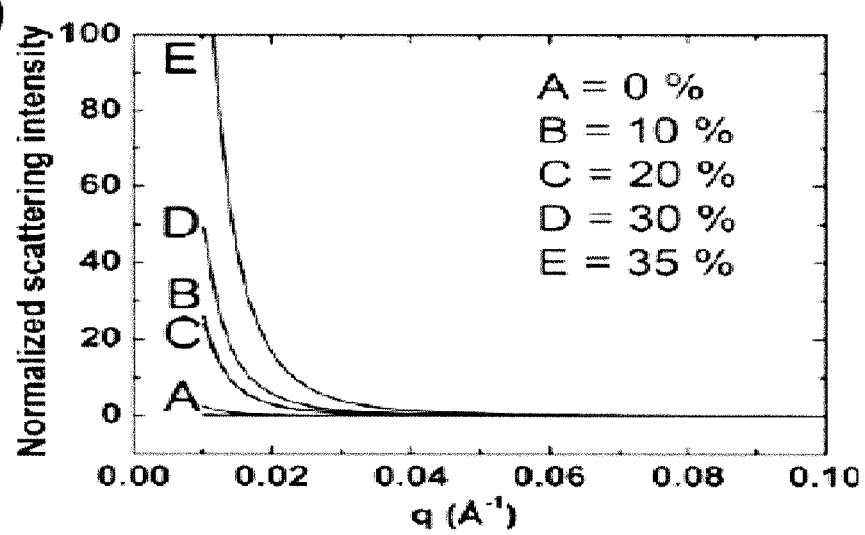

SEQUENCE LISTING

<160> NUMBER OF SEQ ID NOS: 1

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 1
ggtgacgagt gagctactgg gcgg                                          24

APPARATUS AND METHODS FOR LOW TEMPERATURE SMALL ANGLE X-RAY SCATTERING

CROSS-REFERENCE TO RELATED APPLICATIONS

This application is a U.S. national phase filing of PCT/US2013/044088, filed Jun. 4, 2013 and claims the benefit thereof, which claims priority to U.S. Provisional Application No. 61/655,210 filed Jun. 4, 2012, the subject matter of which is incorporated by reference in its entirety.

STATEMENT OF GOVERNMENT RESEARCH

This invention was made with government support by: (1) the National Science Foundation under project No. DMR-0805240; (2) The United States National Institutes of Health under project No. R01 GM65981; and (3) The United States National Institutes of Health under project No. R01 GM085062. The United States government has certain rights in the invention.

The invention pertains to the field of biotechnology. More particularly, embodiments of the invention pertain to apparatus and methods for performing small angle X-ray scattering (SAXS) at low temperatures; most particularly, for determining the structure of and changes in the structure of proteins, DNA, RNA, and other biological molecules and biomolecular assemblies and structures.

In the last decade, small angle X-ray scattering (SAXS) has risen to the forefront of experimental techniques for rapidly obtaining low-resolution structures of biological macromolecules and macromolecular complexes. In this technique, a dilute (typically 1-10 mg/ml, and occasionally down to 0.1 mg/ml and up to 30 mg/ml) solution of, e.g., protein, DNA, RNA, protein complexes, protein-nucleic acid complexes, or even viruses, in an appropriate buffer is irradiated with a monochromatic beam of X-rays. The resulting X-ray diffraction pattern is recorded using an electronic area detector placed a substantial distance (typically one to several meters) from the sample. The detector records X-rays that are diffracted/scattered through small angles (typically from approximately 0.05° to 3°) relative to the direct, unscattered portion of the beam. Since the biomolecules are randomly oriented and the number of molecules illuminated by the X-ray beam is large, the diffraction pattern is symmetric about the direct beam direction, and the data can be reduced to a plot of diffracted intensity I versus scattering angle $2\theta$ or scattering wave vector $q=4\pi \sin(\theta)/\lambda$. Plots of $I(q)$ are generally smooth curves with some "wiggles" or oscillations. By fitting these curves, information about the large scale structure of the biomolecule—e.g., its size and shape (but not the precise positions of its constituent atoms) can often be deduced.

The greatest strength of SAXS is its ability to report structures from macromolecules in solution, without the need for crystallization or labeling; the macromolecules need only be soluble and in a homogeneous, monodisperse phase. Most synchrotron X-ray sources have dedicated SAXS beamlines, including high throughput stations with automated sample loading. Data analysis suites such as ATSAS from the European Molecular Biology Laboratory (EMBL) enable rapid and comprehensive interpretation of SAXS data, yielding information ranging from radius of gyration through structural envelopes. This information is used in studies of conformational/structural changes in response to substrate binding, of ligand binding and complex formation, and in determining initial phases for X-ray crystallographic determination of molecular structure.

Problems with SAXS as Applied to Biomolecules

The biggest challenges in biomolecular SAXS are well known. The first is the difficulty of preparing solutions that are fully monodisperse and free of any aggregates or other larger objects that can corrupt the SAXS signal, especially at low q values. This monodispersity must be maintained throughout SAXS data collection. Biomolecule solutions often begin degrading and aggregating immediately after they prepared. Consequently, samples must be filtered to remove aggregates immediately prior to SAXS measurements, adding cost and complexity to SAXS setups and causing loss of (often expensive) protein. Data must also be collected in as short a time as possible after filtration, which in practice means that freshly filtered sample must be continuously provided (by flow) during measurement and/or that the data must be collected using the intense X-ray beams available only at synchrotron X-ray sources (national facilities to which access is granted via a proposal mechanism) rather than using the much less intense commercial X-ray sources located in the laboratories of individual research groups or in local research facilities.

The second challenge is that the radiation used to measure a sample also disrupts the sample, damaging the biomolecules. SAXS signals are particularly sensitive to radiation-damage-induced molecular aggregation. The maximum tolerable X-ray dose (energy per unit mass) is generally orders of magnitude smaller than in, e.g., crystallography: lysozyme solutions show excessive aggregation for X-ray doses above about 400 Gy (~1 kGy if glycerol is used to modify protein-protein interactions), whereas lysozyme crystals can withstand ~1 MGy at room temperature. As a result, large sample volumes must be irradiated to achieve adequate signal to noise, either by defocusing the X-ray beam or by flowing or oscillating the sample through the beam. For a typical protein at 1 mg/ml concentration, the minimum sample consumption is roughly 12 µl. However, optimal sample volumes and allowable doses are highly sample-dependent, and must be determined on a case-by-case basis.

Radiation damage is also a problem in macromolecular X-ray crystallography (MX) and electron microscopy (EM). There, radiation damage and minimum sample volumes required for structure determination are dramatically reduced by cooling samples to temperatures near 100 K. Solvent and radical diffusion are all but eliminated, and scaffolding by the frozen solvent network prevents large radiation-induced structural relaxations. In MX, crystals can withstand a roughly molecule-independent maximum dose of ~30 MGy, roughly 20 to 150 times larger than at room temperature.

For successful cryocooling, macromolecular structure must be preserved and ice nucleation and growth must be prevented. Solvent vitrification can be achieved by rapid cooling (e.g., by plunging in liquid nitrogen or propane or insertion in a cold gas stream) or by cooling under high pressure. Required cooling rates can be reduced using chemical cryoprotectants such as glycerol. Although initially developed to reduce radiation damage, sample cryocooling also greatly simplifies sample storage and shipping and dramatically increases sample shelf-life. It has transformed protein crystallography, enabling high throughput methods including remote, robotically assisted synchrotron data collection on mailed-in samples.

The potential of cryocooling for SAXS studies has long been recognized, but the critical challenge of reproducibly preparing and collecting data from suitable samples has not been successfully addressed. Unlike crystallography, SAXS is fundamentally a difference technique. The large contribution of solvent to the total scattering from a dilute solution must be subtracted to determine the macromolecule's scattering profile. In standard (room temperature) SAXS practice, this is achieved by collecting and subtracting data from a macromolecule solution and from a macromolecule-free but otherwise identical buffer solution, both in the same fluid cell. Unlike in protein crystallography, any electron density fluctuation on the 0.5-100 nm scale contributes to the SAXS signal. Sample inhomogeneities including macromolecule aggregates and ice crystallites modify the SAXS profile, and can completely overwhelm all other contributions even at small concentrations. The use of cryocooling in SAXS has proven extremely challenging because ice formation causes irreproducible perturbations in SAXS profiles, and because measurements from independent samples must be subtracted to correct for solvent scattering.

For cryo-SAXS to be a viable technique, methods are required that yield reproducibly vitrified and homogeneous samples, that do not significantly alter the macromolecule's structure, and that enable the accurate buffer and background subtraction required for, e.g., molecular envelope determination.

SUMMARY OF THE INVENTION

We have demonstrated methods, devices and systems that have allowed the first successful application of SAXS to cryocooled samples of biomolecules. We have integrated an open-flow nitrogen cryocooler into a SAXS beamline, made modifications to the beamline to improve SAXS data quality and facilitate subtraction of background scattering, and used SAXS to identify cryoprotection and cooling conditions that yield complete vitrification of small drops cooled in the nitrogen gas stream, with cryoprotectant concentrations that do not disrupt molecular structure. We have developed a variety of different designs for sample cells to hold samples for cryo-SAXS that are optimized to yield rapid cooling to cryogenic temperatures, that yield high quality SAXS data from cryocooled samples, and that allow accurate subtraction of background SAXS signals from those due to the biomolecule itself.

As a demonstration of the efficacy of our inventions, using vitrified samples and prototype sample holders, we obtained scattering patterns from glucose isomerase (a standard SAXS reference), and verified that low temperatures protect the molecule from radiation damage without altering its structure. No radiation damage is observed after doses as large as 3.7 MGy, at least two orders of magnitude larger than can be sustained at room temperature. We also showed that useful cryo-SAXS data can be collected from a variety of macromolecules using very small sample volumes—as small as 15 nanoliters. These devices and methods should be especially valuable for highly radiation sensitive samples and when available sample volumes are limited. Once samples are cooled to cryogenic temperatures, all aggregation and degradation ceases. Samples can then be stored indefinitely, and can be easily shipped to, e.g., a remote synchrotron source for measurements. This will allow a large expansion in SAXS studies of biomolecules, and enable high-throughput SAXS structure determination.

BRIEF DESCRIPTION OF THE DRAWINGS

FIGS. 2(a), (b) and (c) show top, left side, and front views of a cryo-SAXS sample cell according to an exemplary embodiment of the invention. The arrow indicates the direction of travel of X-rays through the cell.

FIGS. 5(a), (b), and (c) show top, left side, and front views of a cryo-SAXS sample cell according to an exemplary aspect of the invention, incorporating two cells on a single base. The arrow indicates the direction of travel of X-rays through the cell.

FIGS. 7(a) and (b) show front and side views of a sample cell support in one embodiment of the present invention. FIGS. 7(c) and (d) show front and side views with the sample cell held in place by the sample cell support, according to an illustrative embodiment.

DETAILED DESCRIPTION OF NON-LIMITING, EXEMPLARY EMBODIMENTS

Embodiments of the invention include a system for cryo-SAXS measurements; methods for preparing biomolecular samples for cryo-SAXS measurements, measuring cryo-SAXS data, and analyzing this data to determine information about biomolecular structure; and sample cells and holders designed for rapid cooling of biomolecular solutions to ice-free states and for cryo-SAXS measurements.

Systems for Cryo-SAXS Measurements

Figure 1:
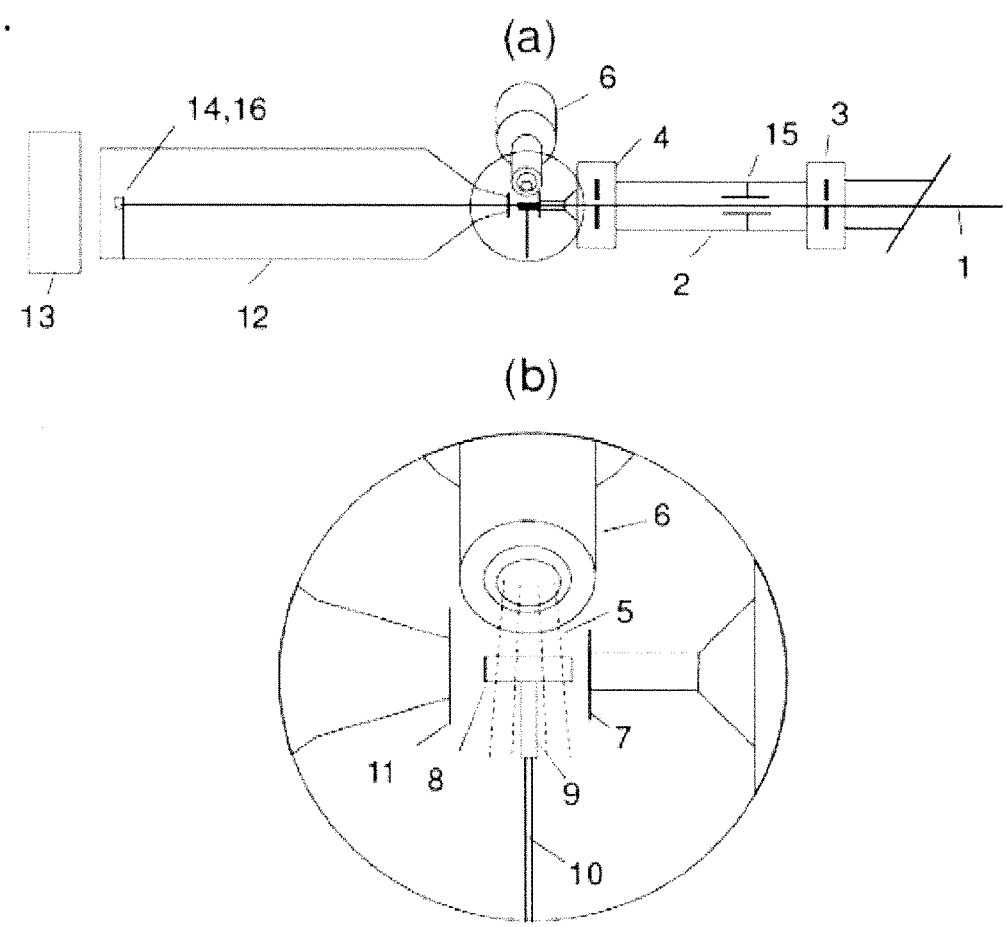
FIGS. 1(a) and (b) show an apparatus for collecting SAXS data from cryocooled solutions containing biological molecules, according to an embodiment of the invention. The arrow indicates the direction of travel of X-rays through the cell.

FIG. 1 shows a system for measurements of small-angle X-ray scattering from biomolecular solutions at cryogenic temperatures. This system is based on experimental setups used in conventional SAXS on liquid samples, but modified in critical ways to enable measurements at cryogenic temperatures and to allow complications associated with cryo-SAXS samples to be addressed. X-ray beam 1 is produced by an X-ray source (a synchrotron source, a rotating anode source, a tube source, or a liquid metal jet source), and may pass through a monochromator (e.g., a single crystal or multilayer monochromator) to produce a beam with a well-defined peak X-ray energy (typically near 8-10 keV) and a desired spread in energies (typically 2% or less of the peak energy.) This beam passes to the sample through an upstream flight tube 2, which may be evacuated or filled with helium. The upstream flight tube reduces scattering of the X-ray beam as it passes from source to sample.

Slits or apertures 3 and 4 are used to define the size and shape of the beam that reaches the sample (to match the sample and sample cell dimensions), and to block X-rays scattered by interactions with gas and system components upstream of each slit or aperture, that otherwise may contribute to X-rays measured at the area detector 13. The first "beam defining" slit/aperture set 3 defines the X-ray beam size and shape that is transmitted to the sample. The second "guard" slit/aperture set 4 is set to a size slightly larger than the beam transmitted through slit set 3, and blocks X-rays scattered upstream of slit/aperture 3 that traveled obliquely through that aperture, as well as X-rays scattered by slit/aperture 3 itself. A typical beam size at the sample may be from 2 mm to as little as 10 μm, depending upon the sample cell size and the X-ray optics.

In conventional SAXS measurements, the sample cell is in vacuum, to reduce X-ray scattering by gas outside the sample cell. For cryo-SAXS, samples could be mounted on the end of a cryogenically cooled stage that is in vacuum, but this would complicate sample changing and make high throughput cryo-SAXS measurements challenging.

In the exemplary system, the sample's temperature is maintained at cryogenic temperatures during SAXS data collection by placing the sample within a cryogenic temperature stream of flowing gas 5, which may be generated by a gas stream cryocooler 6. The gas may be nitrogen or, for lower scattering of X-rays, helium. Suitable cryocoolers manufactured by, e.g., Oxford Cryosystems, are used in cryocrystallography. Suitable cryogenic temperatures are below 180 K (to prevent ice formation on normal SAXS measurement timescales), and, advantageously, below 140 K (roughly the temperature at which pure water forms a glass and remains glassy without ice crystals forming for an indefinite time). Standard nitrogen gas stream cryocoolers typically operate at 100 K.

The sample end of the upstream flight tube is terminated by a gas impermeable window 7. This window should be thin—much thinner than the X-ray attenuation length in the material from which the window is made—to minimize X-ray beam attenuation and scattering by the window. It should also have surfaces that are free of surface roughness on length scales of ~1 to 100 nm, corresponding to the range of q values of interest in SAXS measurements, so that the windows do not produce appreciable small-angle X-ray scatter. For example, the windows may be made of $Si_3N_4$ with a thickness of 200 nm.

The second slit/aperture set 4 may be located within the upstream flight tube 2. It may also be located between the upstream flight tube window and the sample, including on the sample cell itself, to minimize the amount of parasitic small angle scatter transmitted through it from sources upstream of it.

The X-ray beam emerging from the upstream flight tube then passes through a sample cell 8 containing the sample. The sample cell 8 may be attached via a supporting frame 9 that is connected to a rod or post 10. The sample cell, supporting frame and rod are attached to a sample stage (not shown) that allows positioning and possibly also orientation of the sample in the X-ray beam. To simplify attachment to the sample stage, the supporting frame and rod are preferably compatible with magnetic goniometer bases used in high throughput cryocrystallography, and with sample stage heads that accept magnetic goniometer bases.

The direct X-ray beam and X-rays scattered by the sample and holder then proceed through a downstream window 11 (similar to the upstream window 7) and an evacuated downstream flight tube 12 (to minimize scattering of the direct beam) to an area detector 13 (e.g., a CCD detector or a pixel array detector, such as those manufactured by Rayonix and Dectris). The area detector is typically located from one to several meters from the sample, so that its area captures only X-rays scattered through small angles.

A beam stop 14 of size at least slightly larger than the direct X-ray beam diameter absorbs and attenuates the direct beam so that the beam intensity at the detector does not saturate it, while allowing X-rays scattered by the sample through small angles to reach the detector.

The direct X-ray beam intensity may be monitored using two detectors, one located upstream of the sample 15, and one located downstream of the sample, with the downstream direct beam measurement configured so as not to obstruct scattered X-rays. The ratio of the beam intensities at the positions of these two detectors gives the attenuation of the X-ray beam by the sample, sample cell, and other components along the beam's path. It thus depends on the X-ray beam's path length through the sample, and for samples of the same composition, can be used to determine this path length. These two detectors may be cross calibrated using a reference sample, and will advantageously have very low drift to allow accurate (better than 0.1%) relative intensity measurements.

Suitable upstream detectors include a helium gas ionization chamber detector. Suitable apparatus for measuring the downstream beam intensity include a PIN diode detector directly incorporated into the beam stop 16. A calibrated beamstop that attenuates but does not fully block the direct beam can be used, so that area detector 13 can be used to measure the direct beam intensity. The beam stop may be designed to reflect some fraction of the direct beam into an off-axis detector (e.g., an X-Flash detector, a photomultiplier tube) that points toward the beam stop surface.

Methods for Cryo-SAXS Measurements

The methods required for cryo-SAXS on solutions of biomolecules cooled to cryogenic temperatures differ from those used in conventional, near room-temperature measurements in several important ways. The samples must be cooled to cryogenic temperatures and held at cryogenic temperatures until measurements are complete. They must be cooled in such a way that no ice or other inhomogeneities on 1 to 100 nm length scales probed in SAXS form during or after cooling are formed. This is considerably more challenging than, e.g., cooling protein crystals to cryogenic temperatures for cryocrystallographic measurements because SAXS data is far more sensitive to the presence of even minute amounts of ice than are crystallographic data.

Minimizing ice formation requires that cryoprotectants such as ethanol, glycerol, ethylene glycol, polyethylene glycol, polypropylene glycol, sucrose or trehalose be added to the solutions. At high concentrations, cryoprotectants can change the structure of biomolecules. Cryoprotectant concentrations should thus be limited to below 60% w/w, and, more advantageously below 40% w/w. Our experiments show that achieving ice-free samples at such concentrations requires sample cooling rates comparable to or in excess of 100 K/s. Achieving these cooling rates requires the use of small samples—generally, volumes less than 10 microliters and typically less than 1 microliter; the use of sample cells with low thermal mass and good thermal conductivity; and the use of cooling methods that maximize the rate of heat transfer throughout the cooling process. The samples in general will contract or expand on cooling, and so sample cells must be designed to withstand the forces exerted upon them due to this expansion and contraction.

On the other hand, radiation damage to the sample by the illuminating X-rays is dramatically reduced, so that much smaller sample volumes—100 to 1000 times smaller than in conventional room-temperature SAXS measurements—can be used. The flow cells used in room-temperature SAXS are then replaced with much smaller volume, non-flow cells that can be rapidly cooled to cryogenic temperatures.

The biomolecules and biomolecular structures of interest in SAXS and cryo-SAXS include proteins, nucleic acids (DNA and RNA), protein complexes, protein-nucleic acid complexes, and larger structures such as virus capsids.

As in conventional SAXS measurements, in cryo-SAXS a monodisperse, aggregate-free solution of the biomolecule or complex of interest is prepared. Generally, this requires preparing a suitable buffer solution containing salts and other constituents to solubilize and stabilize the protein, and to prevent it from aggregating or precipitating. Maximum biomolecule concentrations are generally limited to below 10 mg/ml (depending upon the second virial coefficient describing intermolecular interactions in solution), to minimize effects on SAXS signals due to interparticle interference.

Unlike in conventional SAXS, in cryo-SAXS cryoprotectants are added to this buffer solution to reduce the cooling rates required to prevent ice formation and to achieve a homogeneous, ice free state at cryogenic temperatures. Cryoprotectant free protein containing buffer solutions require impractically large cooling rates of approximately $10^6$ K/s to prevent ice formation. With cryoprotectant concentrations of ~50% w/w, the required cooling rates are reduced to roughly 10-50 K/s. However, large cryoprotectant concentrations (especially above 50% w/w) may alter the biomolecule's structure. Concentrations in the range of 40% w/w and lower are thus advantageous, which may require cooling rates of at least several hundred K/s.

Cryoprotectants also modify the average electron density difference or "contrast" between the biomolecules and the surrounding solution. This contrast determines the strength of the SAXS signal from the biomolecule, and proper choice of cryoprotectant or of a mixture of two or more cryoprotectants can maximize this electron density contrast. Contrast maximizing choices include the chain polymers polypropylene glycol and polyethylene glycol, which have electron densities of 332 and 386 electrons per cubic nanometer, comparable to that of water (334 electrons per cubic nanometer) and lower than those of most other common, biomolecule-friendly cryoprotective agents.

After the biomolecule is dissolved in the cryoprotectant-containing buffer, the solution is usually centrifuged or filtered using standard methods (e.g., using size-exclusion chromatography) to eliminate aggregates.

In cryo-SAXS, this solution is placed into a sample cell. The sample cell is optimized both to yield the cleanest SAXS data and to allow the fastest possible cooling of the sample, as discussed below. The sample cooling rate is ultimately limited by the sample volume and by its geometry (e.g., its surface area to volume ratio). Typical solution volumes in cryo-SAXS will be less than 10 microliters and advantageously less than 1 microliter in order to cool fast enough that cryoprotectant concentrations below 50% w/w will yield ice-free state at cryogenic temperatures. Experiments described later indicate that volumes as small as 10 nanoliters are sufficient to determine a molecular structure. The smallest feasible volume for a molecular structure determination using a single sample is determined by the amount of SAXS data that can be obtained before radiation damage to the sample becomes significant, compared with the amount of SAXS data required to determine a molecular structure. In principle, volumes as small as 1 pl ($10^{-12}$ liters) may be used with a synchrotron X-ray beam that is focused or defined using apertures to, e.g., a 5 μm diameter, and using a cell thickness along the X-ray beam that is much smaller than the X-ray absorption length in the sample. For example, a cell with interior dimensions of 10 μm×10 μm×10 μm has a volume of 1 pl. However, data from measurements on multiple samples would then need to be combined to obtain enough data to determine the molecular structure, and errors introduced by sample irreproducibility might then make accurate molecular structure determination difficult.

Once the sample has been dispensed into the sample cell (e.g., using a pipette, a syringe, an automated liquid handler, an acoustic drop generator), the sample and cell are cooled to cryogenic temperature at a rate of at 100 K/s or larger. Reference is made to PCT/US2007/007963, 20090133410, "System and method for increased cooling rates in rapid cooling of small biological samples," the subject matter of which is fully incorporated by reference. The cell is loaded and cooled as soon after sample filtration as is feasible (e.g., in one minute or less) to limit aggregation and also any deposition of biomolecule on the cell walls that may reduce biomolecule concentration.

The sample may be cooled by inserting it into a cryogenic temperature stream of nitrogen or helium gas, including in the gas stream that is used to maintain the sample at cryogenic temperature during SAXS data collection. It may be cooled by plunging it into a cryogenic liquid such as liquid nitrogen, liquid propane, or liquid ethane, preferably held at temperatures just above their melting temperature. It may be cooled by "slamming" it onto a cryogenic temperature surface of a high thermal conductivity material such as copper. One advantageous method is to cool the sample and cell by plunging them into a liquid cryogen (nitrogen, propane or ethane) at a speed of roughly 1 m/s, where the cold gas layer that forms immediately above the cold liquid is removed prior to the plunge by blowing it away. This method gives the fastest possible cooling rates, approaching 10,000 K/s for 1 nl samples, as discussed in US Application 20090133410, the subject matter of which is fully incorporated herein by reference. These large cooling rates allow sample cryoprotectant concentrations needed to prevent ice formation to be minimized.

After cooling to cryogenic temperatures, aggregation and sample degradation are impossible as long as the sample is maintained at temperatures below its glass transition temperature (roughly 140 K for pure water, and higher for water-cryoprotectant mixtures). In practice, temperatures below 150 K are sufficient, and so samples can be stored indefinitely in liquid nitrogen. This long sample storage time is a large advantage of cryo-SAXS over conventional SAXS on liquid samples. Many samples can be frozen and stored over an extended time period, and then measured as a group at, e.g., a synchrotron source, without concern for sample aggregation or degradation.

For SAXS measurements, the sample is transferred from its storage container (or from the cryogenic temperature liquid or gas) to a cryogenic temperature stream of nitrogen or helium gas (5 in FIG. 1), which may be generated using a standard gas stream cryocooler (6 in FIG. 1) used in cryocrystallography. Typical nitrogen cryocooler streams have temperatures of 100 K. The sample temperature must not rise above its glass transition temperature during transfer from its storage container or liquid cryogen to the gas stream. This can be achieved by enclosing the sample in a cryogenic temperature cover or by keeping it immersed in, e.g., liquid nitrogen during the transfer. Transfer and sample positioning in both the cryostream and the X-ray beam are facilitated by attaching the sample cell to a standard goniometer base used in cryocrystallography, which can then be attached to a standard stage such as those used in cryocrystallography for positioning and orienting the sample in the X-ray beam.

The sample is then illuminated with an X-ray beam 1, and the scattered X-rays measured using the area detector 13. At the same time, the direct beam intensity can be measured to high accuracy before and after the sample using detectors 15 and 16.

A second, reference sample is prepared, dispensed into a sample cell, rapidly cooled to cryogenic temperature, and then examined using cryo-SAXS. The reference sample does not contain the biomolecule of interest, but is otherwise identical in composition to the first sample. This sample may be dispensed into the same cell as the first, biomolecule containing sample, or it may be dispensed into a different cell.

Figure 10:
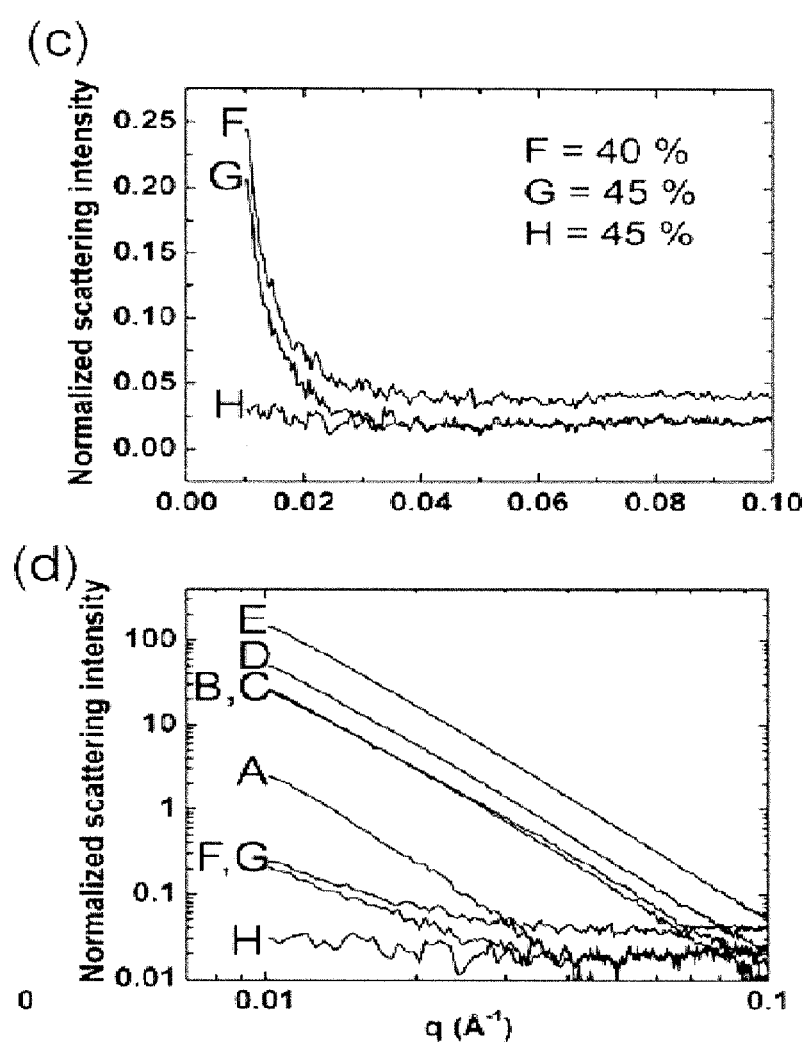
FIG. 10. (a) Photographs of ~1 microliter drops of PEG 200-water mixtures held in ~700 μm nylon loops after cooling to 100 K in a $N_2$ gas stream. PEG concentrations for drops (A-H) ranged from 0% to 45% (w/w). (b) and (c) SAXS curves acquired from the drops in (a). (d) The data of (b) and (c) on log-log axes.

Cryo-SAXS data from both the biomolecule containing and reference samples are examined to verify that both samples are ice free and free of other inhomogeneities induced by cooling. This can be assessed by examining the scattered intensity at small q, especially for the reference sample. As discussed below and as shown in FIG. 10, ice produces large increases in the small q scattering. This increase is most easily detected in the reference sample, as there are no small q contributions to the scattered intensity from biomolecules. The scattering intensity at low q (e.g., 0.01 Å$^{-1}$) should be less than a factor of two larger than that at high q (e.g., 0.1 Å$^{-1}$), and at most a factor of five larger. Provided that the sample cells and cooling methods are reproducible, examination of the reference sample SAXS data should be sufficient to assess whether both samples have been successfully cooled without ice formation.

If the sample cells are designed so that the path length of the X-ray beam through each sample is accurately and reproducibly fixed, then the SAXS data on the biomolecule containing and reference samples can be analyzed using methods standard in (room temperature) SAXS to determine the scattered intensity versus wave vector due to the biomolecule itself, and then to determine information about the biomolecule's structure.

If the sample cell dimensions do not control or determine the path length of the X-ray beam through each sample (i.e., if the dimension of each sample along the X-ray beam path is not fixed), then this path length must be deduced for both the reference sample and biomolecule containing sample, or the path length ratio must be deduced. This ratio allows the measured scattered X-ray intensities versus wave vector q to be properly normalized, and for the normalized intensities from the biomolecule-containing and reference samples to be analyzed to determine the scattered intensity versus wave vector q for the biomolecule itself. This normalization can be performed by measuring the direct beam intensity before and after the sample, for each sample. The ratio of these intensities determines the attenuation factor for each sample, which is determined by the X-ray path length through each sample.

Errors in this normalization procedure result if the sample boundaries where the beam enters and exits it are not flat and perpendicular to the beam over the area of the beam's cross-section. Thus, methods for flattening the sample boundary are useful. When the sample boundary is a meniscus formed due to contact with cell walls, the boundary can be flattened by pinning its contact lines using ridges on the interior surface of the sample cell, as discussed below, and by dispensing an accurately determined volume into the cell, just sufficient to produce a flat meniscus at the position of the contact line pinning ridges. The sample boundary can also be flattened by spinning the sample about its center of mass before and during cooling at a sufficient speed that the internal pressure generated by the spinning greatly exceeds the capillary pressure associated with surface tension responsible for curvature of its surface.

Sample Holders for Cryo-SAXS Measurements

The cells used to hold the biomolecule-containing and reference samples during cooling to cryogenic temperature and during cryogenic temperature SAXS data collection are a critical element in successful cryo-SAXS measurements.

Conventional room-temperature SAXS measurements require large sample volumes to obtain sufficient data to determine a biomolecular structure. At room temperature, samples are damaged by relatively small X-ray doses (where dose is X-ray energy deposited per kg of sample). This sets a minimum sample volume required to determine a molecular structure that is typically at least 10 microliters and often much more. SAXS systems typically use a continuous flow cell that is fixed in place in the SAXS/X-ray apparatus. Each sample to be examined is flowed through the cell while X-rays illuminate a part of the cell. As sample flows through the X-ray beam, it becomes damaged, and the flow carries the damaged sample out of the beam. After each sample solution is measured, the cell interior is "washed" with an appropriate solution. The flow cells are often held in vacuum, so that removing them for cleaning and maintenance requires some effort. The cells must have two X-ray transparent windows bounding the liquid sample, whose size must be comparable to or larger than the X-ray beam used to examine the sample.

Generally, biomolecule-containing solutions are transported to the SAXS setup (a small laboratory system, or a system at an X-ray beamline at a synchrotron X-ray source such as the Advanced Photon Source at Argonne National Laboratory) and then injected into the setup's fixed sample cell. Sample solutions, not sample holders loaded with sample solutions, are thus transported to the X-ray source/SAXS setup for measurements, and few sample cells are required.

In both conventional SAXS and cryo-SAXS, the dimension of the sample cell and sample along the X-ray beam is typically chosen to most efficiently use the available X-ray photons in the X-ray beam to generate SAXS signal from the sample. Generally, the sample cell dimension is chosen to be comparable to the X-ray attenuation length in the sample solution at the chosen X-ray energy. This length increases from approximately 1 mm at 8 keV to 2 mm at 10 keV.

In cryo-SAXS, to achieve the sample cooling rates of ~100 K/s or greater needed to prevent ice formation (while using cryoprotectant concentrations that are not so large as to change the biomolecule's structure), the sample cells must have small volumes—preferably less than 1 microliter—and must be designed to minimize the cell's heat capacity and maximize the rate of heat transfer from the cell during cooling in a cryogenic temperature liquid or gas stream. Preferably, the cell's heat capacity should be small (less than 1 mJ/K) compared with the roughly 4 mJ/K heat capacity of 1 microliter of water (although a cell design with a large aspect ratio and large surface area to volume ratio could have a larger cell heat capacity). Our experiments show that cooling to cryogenic temperatures greatly reduces radiation damage to the biomolecules—by a factor of 100 or more. Consequently, cryo-SAXS allows the same amount of SAXS data to be obtained before radiation damage becomes excessive using a much smaller total sample volume.

To achieve the fastest cooling and to minimize cryoprotectant concentrations, the sample-filled cells are preferably cooled by immersion in a liquid cryogen. The frames or other hardware used to hold the cells during cooling should not appreciably affect these cooling rates. These cells are then transported to the X-ray source/SAXS setup for measurement. Although individual cells could be thawed, cleaned and reloaded with a new sample after measurement of each sample, this would be tedious, and the time spent thawing and cleaning would be long compared with typical SAXS measurement times per sample (~1 second or less at a third generation synchrotron source), and so would be a bottleneck in data collection. Instead, a large number of samples cells are loaded with a large number of reference and biomolecule-containing samples. These samples are then cooled, stored, and transported as a group for rapid sequential measurement on a cryo-SAXS setup.

Consequently, cryo-SAXS sample cells should preferably be easily mass produced at modest cost, should be easy to fill using pipettes and other standard liquid handling hardware, should be easy to cool, and should be easy to transfer from a cryogenic storage container to the sample positioning stage of a SAXS setup. Preferably they are also easily cleaned (e.g., in a detergent solution, in an ultrasonic bath) and/or are of sufficiently low cost that they can be disposed after each use. A substantial infrastructure has been developed to handle cryocooled crystals mounted in nylon loops for X-ray cryocrystallography, and this infrastructure allows high throughput measurements. Sample holders for cryo-SAXS may be designed to be compatible with at least some hardware components of this infrastructure, including the sample holding and positioning stages and the magnetic goniometer bases conventionally used to quickly and easily attach samples to these stages.

In the present invention, we distinguish two different kinds of sample cells for cryo-SAXS: (1) cells in which the solution is bounded in at least one direction by X-ray transparent walls or windows, and in which the X-ray beam is directed through these windows; and (2) cells in which there are no windows, walls or other obstructions along the X-ray beam path, so that the X-ray beam passes only through the sample itself.

FIG. 2 shows one design of a sample holder with X-ray transparent windows or walls along the X-ray beam path. The cell has two parallel walls 17 that project perpendicular to a supporting base 18. The liquid sample is injected into the volume between the walls, so that the liquid contacts both walls and provides a continuous, air-free path for the X-ray beam through the sample between the walls.

The separation between the walls is set to be comparable to the X-ray attenuation length in the sample, to give adequate SAXS signal per incident direct beam photon and to minimize data collection times. This separation will typically be 0.5 to 2 mm and, particularly, about 1 mm, and a maximum range (depending upon X-ray energy and sample absorption) between 0.1 and 5 mm.

These walls are advantageously highly X-ray transparent, which means that their thickness should be comparable to or smaller than the X-ray attenuation length in the wall material. X-ray attenuation lengths at 8 keV are roughly 70, 120, and 70 µm for silicon, silicon dioxide and silicon nitride, respectively. If the walls are too thin, they are easily deflected and/or broken, including by forces exerted during processing required to fabricate the cells, by forces exerted during cleaning of the cells (e.g., by sonication), and by forces exerted by the sample between the walls as the sample contracts or expands during cooling and thawing. For silicon walls, our experiments suggest that walls larger than 15 µm thick reliably survive the processes involved in cell fabrication and cleaning. Large wall deflections—i.e., more than a fraction of 1% of the wall spacing introduce errors when subtracting SAXS signals from biomolecule containing and reference solutions. For silicon walls with heights of a few hundred micrometers, a wall thickness of 10 to 50 µm provides a good compromise between X-ray transparency and rigidity.

The walls should also produce very little X-ray scattering at small angles, so as to minimize background SAXS signals compared with those from the sample itself. Any inhomogeneity or nonuniformity in the walls that varies with position along or perpendicular to the wall surfaces on the length scales probed by SAXS—from roughly 1 to 100 nm—will generate SAXS signals. Consequently, the walls should be as flat and smooth as is possible.

The dimensions of the wall perpendicular to the X-ray beam direction—i.e., the wall height and width—are set by the desired sample volume. For successful ice-free cooling with the smallest cryoprotectant concentrations, this volume, and thus the lateral wall dimensions, should be minimized. As discussed above, it should generally be kept below 1 microliter to give cooling rates of at least 100 K/s and to avoid cryoprotectant concentrations in excess of 50% w/w. For a 1 microliter volume, these dimensions should be less than roughly 1 mm.

In many cases it will be preferable to match the lateral dimensions of the walls to the X-ray beam dimensions, since sample volume outside the beam does not contribute to the SAXS signal. A typical X-ray beam in current practice has a full width at half maximum intensity (FWHM) of roughly 100 μm, although some small amount of intensity may be present (due in part to grazing incidence scattering) to a distance from beam center roughly two or three times this size. A wall height and width of between 100 to 500 μm is advantageous. Total volumes defined by the walls will then be between roughly 0.01 and 1 microliter for a 1 mm cell dimension along the X-ray beam. Smaller volumes—down to 0.001 microliter and possibly smaller—may be feasible when using smaller, more intense X-ray beams available at synchrotron sources, for samples with sufficiently low radiation sensitivity at cryogenic temperatures. A cell for use with a 20 μm micrometer X-ray beam with cell dimensions of 0.5 mm long by 50 μm by 50 μm will have a volume of 1 nl. Sample cells with volumes as large as 10 microliters might yield fast enough cooling to achieve ice free and homogeneous samples for SAXS in some cases, but larger cells are not likely to be useful.

Subject to the thickness and surface smoothness constraints above, the walls may be made of a wide variety of materials including those commonly used in semiconductor and microfluidic devices such as silicon, silicon nitride, silicon dioxide (quartz), graphene, and the polymers SU8, PDMS, PMMA, and polyimide. A variety of anisotropic etching processes have been developed that allow high aspect ratio (tall and thin) walls with nearly atomically smooth surfaces to be fabricated using crystalline materials including silicon. The walls could also be separately fabricated (e.g., by laser cutting thin sheets) and bonded to the base. Availability and cost of processing tools and processes are also an important consideration in materials choice.

The base to which the walls are attached must be thick enough so as to be rigid, but not so thick that its thermal mass and thermal conductance appreciably slow sample cooling. Generally, a thickness of 0.1 to 1 mm should be sufficient. The base may extend beyond the footprint of the walls to facilitate sample cell handling during cooling and data collection. The base need not be X-ray transparent and need not have smooth surfaces. It can be of a variety of materials including standard materials used in semiconductor and microfluidic devices (silicon, silicon dioxide, silicon nitride, SU8 and polyimide). In particular, it can be of the same material as the walls.

This basic cell design can be modified in several ways.

During filling, sample liquid will tend to spread laterally along the walls and around their edges. Liquid spreading outside of the interior volume defined by the walls and base can be inhibited by adding rectangular, trapezoidal or triangular cross section ridges (19 in FIG. 3) at the outer edges of the wall (and possibly also connecting these with a ridge on the base, not shown), to strongly pin the liquid contact lines there. Contact line pinning ridges or rings are discussed in U.S. Pat. No. 7,666,259, which is incorporated herein by reference. Ridges should extend perpendicular to the walls by at least 5 μm to be effective, and could extend much more, although by blocking access to the side of the sample cell such wide ridges would inhibit filling from the side.

The surfaces of the walls can be treated, for example, by oxygen plasma etching, to make the interior wall surfaces hydrophilic, to encourage uniform sample contact with the X-ray transparent walls across the area of the X-ray beam. The exterior surfaces of the wall and base can be treated by silanizing or by applying coatings similar to the commercial product RainX to make them hydrophobic, to prevent sample spreading to these surfaces.

For "free-standing" walls of a given height and width as in FIG. 2, maintaining adequate wall rigidity constrains the minimum wall thickness. By adding buttress supports 20 in FIG. 3 on the outer (and possibly also the inner) face of the walls, the rigidity of the walls can be increased, allowing the wall thickness to be decreased. These supports can be of a different material than the wall, or they can be fabricated with the wall in a single step.

Figure 3:
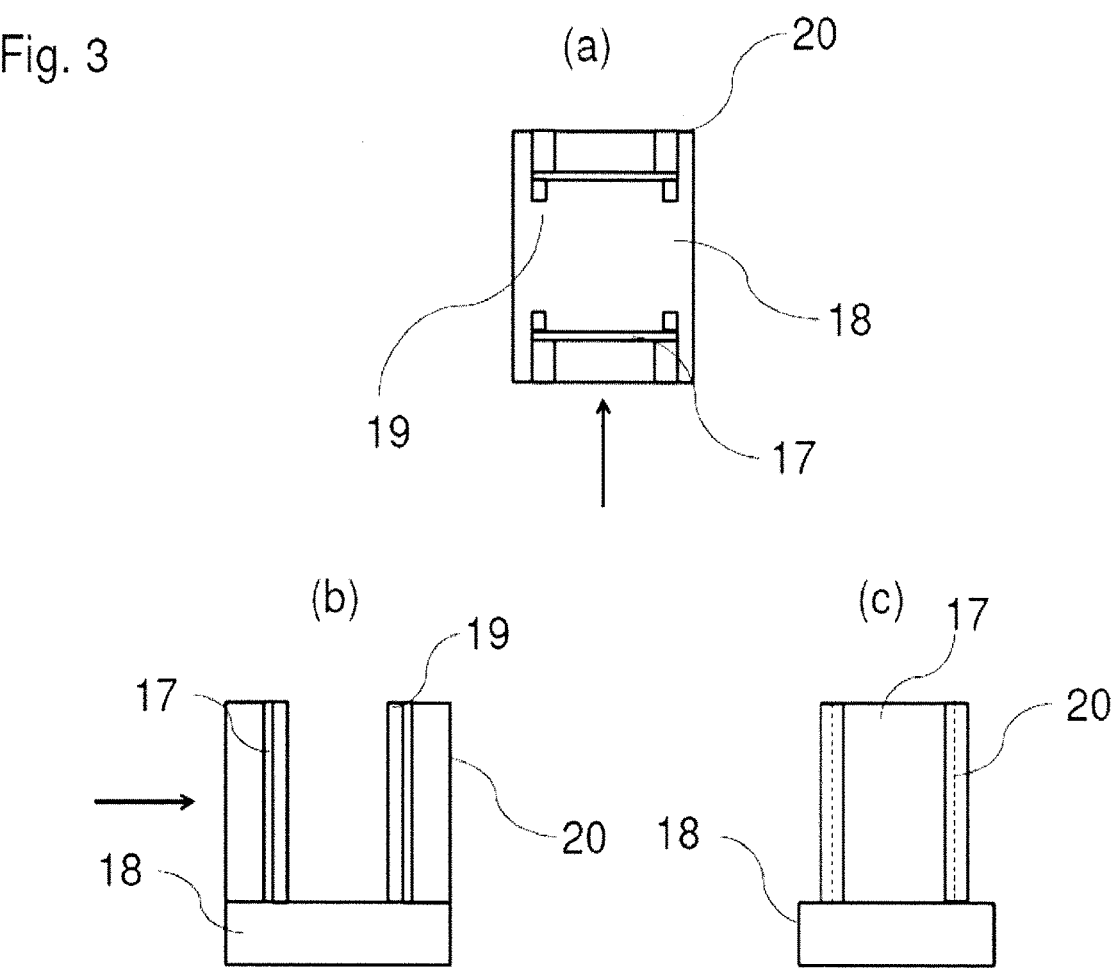
FIGS. 3(a), (b), and (c) show top, left side, and front views of a cryo-SAXS sample cell according to an exemplary aspect of the invention incorporating contact line pinning ridges and wall supports. The arrow indicates the direction of travel of X-rays through the cell.

In the cell designs in FIGS. 2 and 3, the thermal mass of material surrounding the sample is minimized, the area of contact between the sample and the liquid cryogen during cooling is maximized, and the sample is free to expand and contract perpendicular to the walls during cooling and thawing. These factors may be expected to give faster cooling and a more homogeneous low temperature sample state. However, these cells give relatively little control over the final geometry of the dispensed sample.

Figure 4:
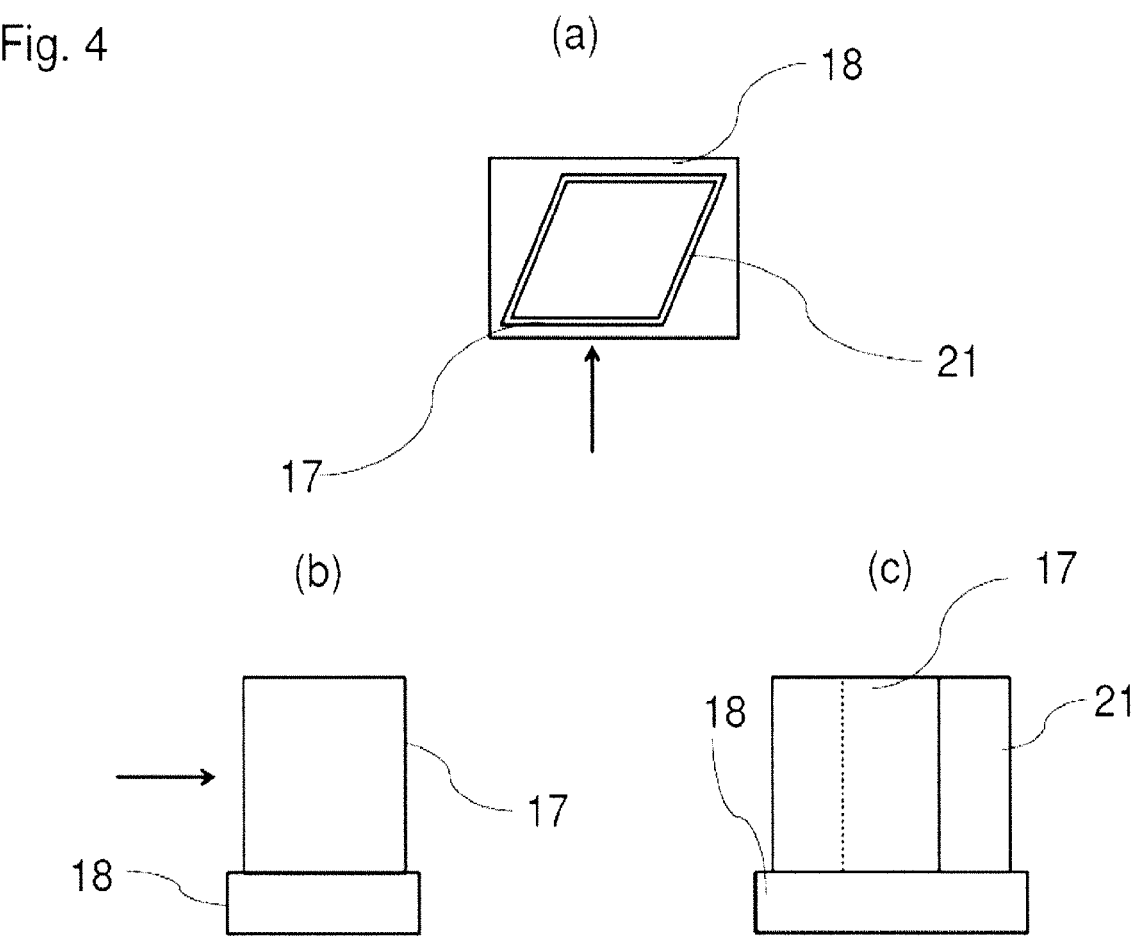
FIGS. 4(a), (b), and (c) show top, left side, and front views of a cryo-SAXS sample cell according to an exemplary aspect of the invention, incorporating continuous side walls connecting the X-ray transparent walls. The arrow indicates the direction of travel of X-rays through the cell.

FIG. 4 shows an alternative design where non-X-ray transparent walls 21 connect the two X-ray transparent walls on either side. These walls confine the sample laterally between the X-ray transparent walls, and also provide structural support for the X-ray transparent walls. The side walls can be perpendicular to the X-ray transparent walls, or at some angle. A deep etching process for generating high aspect ratio walls in silicon (and other crystalline materials) relies on preferential etching along certain crystallographic planes of specially cut wafers. In silicon these planes are not perpendicular, and so the etching process most easily yields side walls at specific, non-normal angles to the X-ray transparent walls, as illustrated in FIGS. 4 and 5.

The sidewall thickness is chosen to maximize heat transfer rates from the sample while a providing adequate cell wall rigidity. They may have thicknesses from 1 to 200 m and, more particularly, in the range 25-50 μm.

FIG. 5 shows that multiple cells can be fabricated on a single base. For example, with two cells, the first can be filled with protein containing solution and the second with reference solution. These can then be cooled, stored and handled together so that their thermal histories and thus the background contributions to their SAXS signals are as similar as possible. A two cell sample holder also allows all data required to determine a biomolecule's structure to be collected using just a single sample holder. The two cells should be close together to minimize sample thermal mass.

Figure 6:
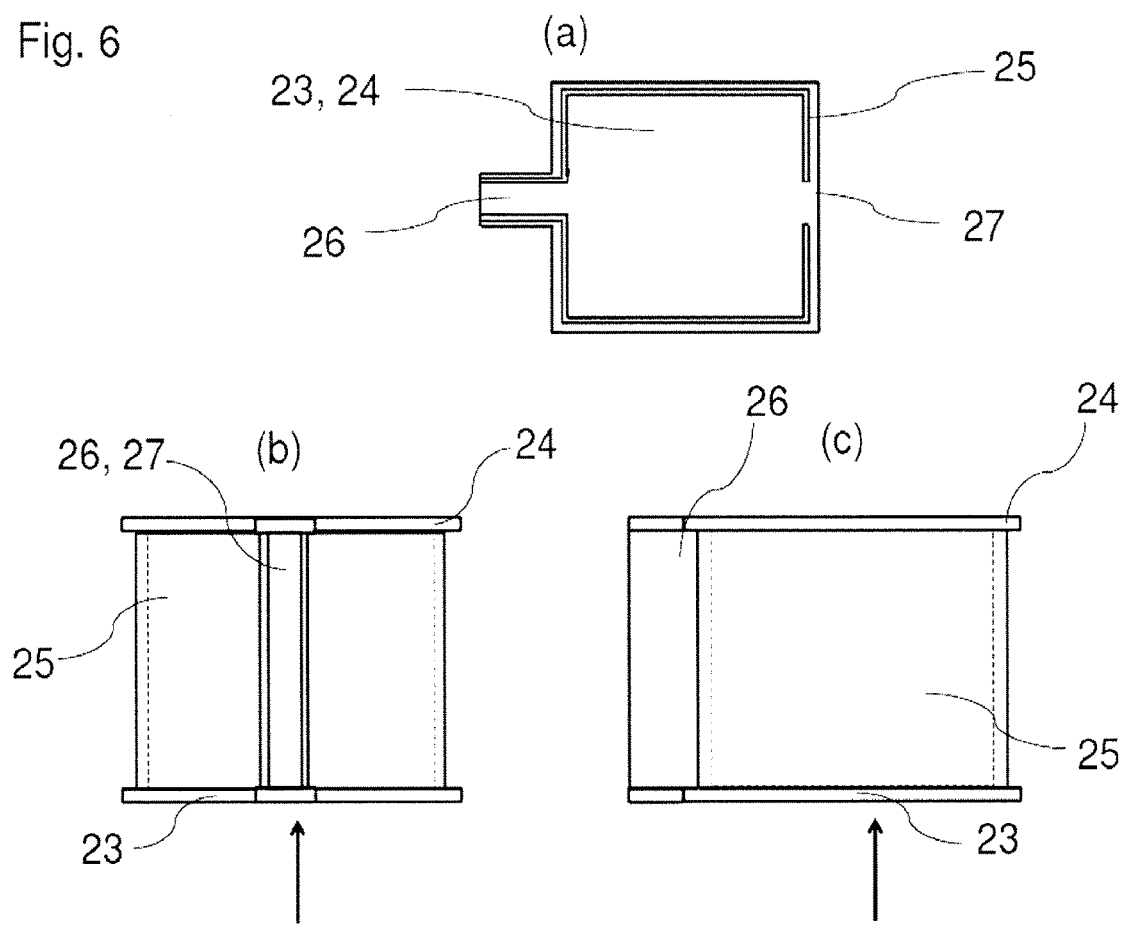
FIGS. 6(a), (b), and (c) show top, left side, and front views of a cryo-SAXS sample cell according to an exemplary aspect of the invention. The arrow indicates the direction of travel of X-rays through the cell.

FIG. 6 shows an alternative cell geometry, in which the X-ray transparent windows 23 and 24 lie in the plane of the base or substrate (such as a silicon wafer). The bottom window 23—e.g., a very thin silicon or silicon nitride wafer or membrane—may form the base. Walls 25 from roughly 10 μm to 2 mm tall (and advantageously comparable to the X-ray attenuation length in the sample, for typical X-ray energies between 0.5 and 2 mm) separate the windows, and may be fabricated on top of this bottom window using, for example, the polymer SU8 (which can be used to generate high aspect ratio features). A separately fabricated window 24 can then be bonded to the top of these walls. Alternatively, the top window could be deposited on top of, e.g., a photoexposable polymer layer in which the walls are to be formed. The walls could be defined by photoexposure through the (very thin) top or bottom window, and the walls then formed by developing and chemical removal of the unexposed (or exposed) material in the polymer layer. The liquid sample is then injected into the cell through an opening 26 in one of the side walls. An additional sidewall opening 27 may facilitate filling. The bottom and/or top window materials may begin in the form of large (compared to the cell size) wafers or sheets. A large number of cells may be fabricated together using these sheets, and then the cells can be separated by scribing and breaking or by laser cutting. Obtaining thin, highly smooth X-ray transparent windows is easier with this geometry than when the windows are fabricated by vertical etching, but cell assembly, involving at least one bonding step, is more complex.

The sample cells described here could be fabricated using processes commonly used for semiconductor and microfluidic devices. All parts but the X-ray transparent windows could also be fabricated using stamping/embossing, micro injection molding, and possibly also 3D microprinting.

In demonstration experiments, we have fabricated silicon sample cells with geometries similar to those shown in FIGS. 2-5 using photolithography and an anisotropic KOH etch. These holders have high aspect ratio vertical sidewalls, 500 μm tall and 20 μm thick. The walls form an enclosed sample holder, 1 mm wide along the x-ray path and slightly wider in the transverse direction. The top of the holders is open to reduce strain on samples during cooling and for ease of loading. The sidewalls are smooth down to a ~5 nm scale.

The sample cells must somehow be held during sample loading, during cooling to cryogenic temperatures, and during data collection. This may most easily and conveniently be done by attaching the cells to a frame or support. This support should be compatible with standard hardware used in crystallography for holding and positioning samples in the X-ray beam. It should also have minimal effect on sample cooling rates, which requires that it have a small thermal mass and/or have a weak thermal connection with the sample.

FIG. 7 shows a design for a sample cell holder. The sample cell 30 slides or snaps into the U-shaped support 28, which can a polymer such as PMMA or other low specific heat, low thermal conductivity material. Alternatively, the U-shaped support may have its interior area covered by a thin supporting sheet to which the sample cell is bonded. The support does not in any way obstruct access of liquid cryogen (or cryogenic temperature gas) to the sample volume and confining walls. Combined with its low thermal conductivity, this ensures that the support will not affect sample cooling. The support is attached to a rod 29, which also has low thermal conductance and is compatible with standard magnetic goniometer bases and with tools for handling these bases during cooling and storage and positioning them in the X-ray beam that are used in biomolecular crystallography. The rods used on sample holders for crystallography are of stainless steel, and have a diameter of approximately 0.65 mm and a length of approximately 20 mm.

Figure 8:
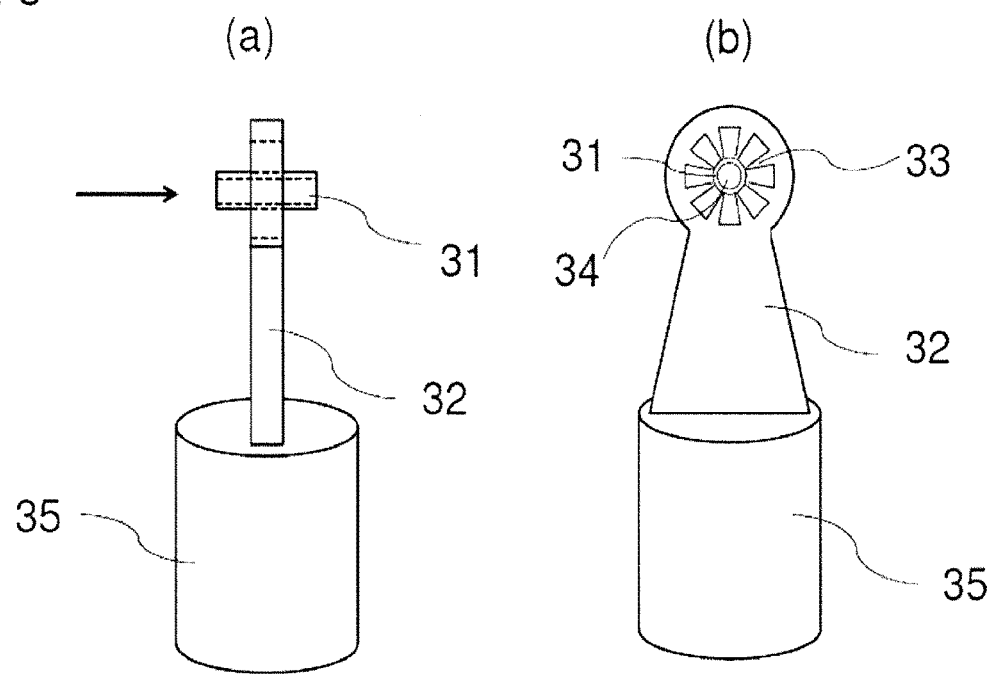
FIGS. 8(a) and (b) show side and front views of a cryo-SAXS sample cell and cell support according to an exemplary embodiment of the invention.

An alternative sample cell design eliminates the X-ray transparent walls, and instead confines the sample between two walls that run parallel to rather than perpendicular to the X-ray beam. The X-ray beam then only passes through the sample and not the holder, so there is no contribution to background scatter from the holder. For example, in the cells of FIGS. 2 and 3, the X-ray beam would be directed through the space between the walls, not through the walls. Consequently, there would be no special constraints on wall thickness uniformity or smoothness. In this geometry, as shown in FIG. 8 the sample cell could be replaced by a simple, thin walled (10-50 micrometer) tube 31, of length 1-2 mm and with a diameter a few times the diameter of the X-ray beam. This sample cell type has been used in initial cryo-SAXS measurements as described below and show in FIG. 9(b). To thermally isolate this tube from the supporting structure and obtain the fastest possible cooling, the supporting structure could consist of a thin, rigid member 32 with a series of narrow, low thermal conductance "fingers" 33 radially disposed around a central opening, and into which the tube 31 was inserted. This thin member may be attached to a rod 35 that is then inserted into, e.g., a magnetic goniometer base. A second identical thin rigid member, displaced along the tube from the first, can used to provide additional support for the tube and prevent it from twisting due to forces exerted by the cold gas stream during data collection. The thickness of each member could then be very small—10-25 micrometers—and so allow for the largest possible cooling rates of the tube and sample within it. However, as noted above and discussed below, analyzing SAXS data to obtain molecular structures is more complicated in this case because the sample thickness along the beam path is not accurately and reproducibly defined.

Initial Studies and Example Applications of Cryo-SAXS

Here we describe our initial studies which led to the first successful demonstration of cryo-SAXS on biomolecules, which illustrate many of the principles and methods discussed above.

Evaluation of Cryoprotectants.

The cryoprotectants poly(ethylene glycol) (average molecular mass of 200 Da), glycerol, and dimethyl sulfoxide (DMSO) were purchased from Sigma (St. Louis, Mo.), and ethylene glycol was purchased from Avantor Performance Materials (Phillipsburg, N.J.). Cryoprotectant-water mixtures were prepared by weight in increments of 5%. Spherical drops of ~1 microliter volume were held in a ~700 μm nylon loop (Hampton Research, Aliso Viejo, Calif.) and rapidly cooled by placing them in a T=100K nitrogen cryostream (700 series, Oxford Cryosystems, Oxford, United Kingdom). Cryo-SAXS data on these gas-stream-cooled samples were acquired at CHESS beamline F2. The X-ray energy was 9.88 keV, the sample-detector distance was 1.47 m and the detector was a fiber-coupled CCD (Quantum 1, Area Detector Systems Corporation, Poway, Calif.). The upstream slits and flight tube were held under vacuum and separated from the sample area by mica windows. SAXS curves were processed using BioXTAS RAW software.

Preparation of Biological Samples for Cryo-SAXS.

Glucose isomerase crystals (Hampton Research, Aliso Viejo, Calif.) were re-dissolved in buffer containing 100 mM Tris pH 8.0 and 1 mM MgCl2. Hen egg white lysozyme (Sigma, St. Louis, Mo.) was dissolved in buffer containing 40 mM Na-acetate pH 4.0, 50 mM NaCl and 1% (v/v) glycerol. A 24-bp DNA duplex with sequence GGTGAC-GAGTGAGCTACTGGGCGG (SEQ ID NO: 1) (and its complement) was made from synthetic HPLC-purified oligonucleotides (Integrated DNA Technologies, Coralville, Iowa). The complementary strands were mixed and annealed to form the duplex, following vendor instructions. The DNA was then buffer exchanged with 10 mM Na-MOPS pH 7.0 and 100 mM NaCl using a spin column (Amicon Ultra-0.5, 10,000 mol wt cutoff, EMD Millipore, Billerica, Mass.). For each matching buffer, a 2×PEG solution was prepared with 946 mg/mL PEG 200. Each 2×PEG solution was combined with the corresponding cryo-SAXS sample and matching buffer in a 1:1 ratio by volume, for a final concentration of ~45% (w/w).

Sample Holders.

Two different window-free, low volume sample cells were used for cryo-SAXS. For ~1 microliter volume samples, the cell (FIG. 9(b)) was comprised of 1.8 mm long, 860 μm ID, 25 μm wall polyimide tubing. To thermally isolate the sample from the stainless steel rod which attached the sample cell to a magnetic goniometer base, the sample holder was glued to a short section of 510 μm ID, 25 μm wall polyimide tubing, which was press-fit over the support. The cell was oriented so that the X-ray beam passed along its axis and through the open ends of the tubing. For sub-microliter volumes samples, the sample was held by surface tension in a standard polyimide crystallography loop with a 600 μm diameter (MicroMount, MiTeGen), shown in FIG. 10(a). For room temperature SAXS measurements, an in-vacuum 2 mm quartz capillary with oscillating flow was used to minimize radiation damage.

SAXS Data Collection.

Figure 9:
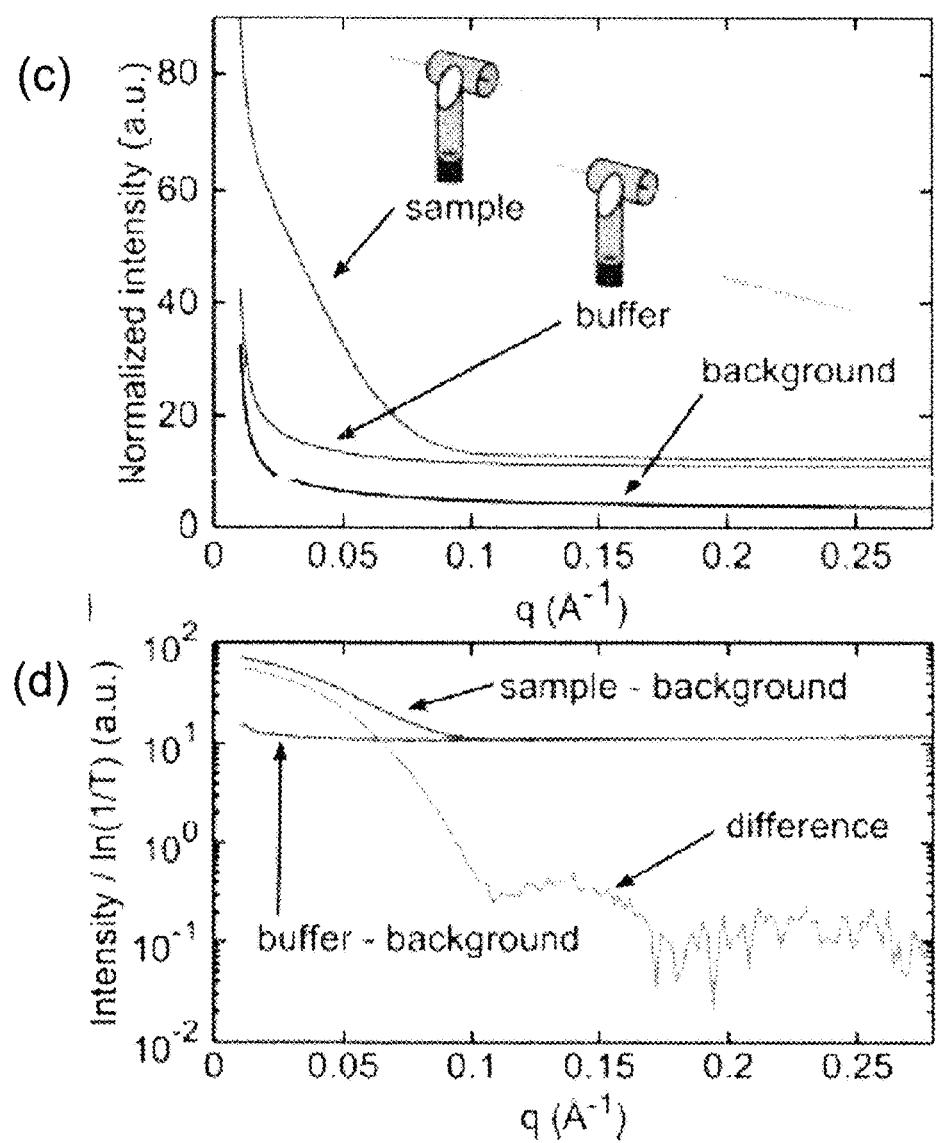
FIG. 9. Apparatus and method for obtaining SAXS profiles from solution samples at 100 K. (a) A SAXS beamline was configured with a cryostream providing a steady flow of T=100K $N_2$ gas at the sample position. (b) A sample in the cryostream between two flight tubes bounded by silicon nitride windows. The inset shows a sample holder. (c) Cryo-SAXS profiles obtained from vitrified solutions of 2 mg/ml glucose isomerase (GI) and its matching buffer, as well as for the instrumental background with the sample removed. (d) Measurement of the X-ray transmission factor, T, and normalization by the path-length, log(1/T), provided accurate background subtraction using the data in (b) to obtain GI's SAXS profile (labeled "difference").

SAXS data from biological samples were collected using beamline G1 at CHESS, configured as shown in FIG. 9(a). The beamline was configured with a low-noise area detector (Pilatus 100 K, Dectris, Baden, Switzerland), a He ion chamber for monitoring the incident intensity, and a PIN diode beamstop for measuring transmitted intensity. Monitors for incident intensity (ion chamber) and transmitted intensity (PIN diode) allowed measurement of the X-ray transmission factor for each sample and normalization of scattering profiles. A cryostream provided nitrogen gas at 100 K for sample cooling (FIG. 9(a),(b)). SAXS data were analyzed using code written in-house in MATLAB (The MathWorks, Natick, Mass.).

Because of the small sample volumes used for cryo-SAXS, background scattering originating upstream of the sample had to be minimized. The upstream flight tube was filled with He and extended to within ~5 mm of the sample using 1.8 mm ID, 0.3 mm wall stainless steel tubing. To further block background scattering that could pass around the sample, the guard slits were supplemented by a 200 nm thick, 500 μm square aperture $Si_3N_4$ window in a 381 μm thick Si frame (Fabrication Services and Technology Ltd, Northampton, England) that was glued to the end of the tubing. Scattered X-rays were collected through an evacuated flight tube with a 200 nm thick, 2 mm square $Si_3N_4$ window with (Fabrication Services and Technology Ltd) epoxied to an aluminum cone at the upstream end. The photograph in FIG. 9(b) shows the position of these windows relative to the sample and cryostream.

SAXS data on biomolecules were acquired at CHESS beamline G1 during two separate runs with similar beamline configurations. In the first run, cryo-SAXS data were taken using the 1 microliter holder. A 1.52 m sample-detector distance and a 10.5 keV X-ray energy were used to probe scattering wavevectors $0.01<q<0.28$ Å$^{-1}$, where $q=4\pi \sin(\theta)/\lambda$, $2\theta$ is the scattering angle and $\lambda$ is the X-ray wavelength. The beam size at the sample position was 119 μm×193 μm (height×width, FWHM). The X-ray flux calculated from the current through an $N_2$ ion chamber, placed at the beamstop position with the sample removed, was $6.3\times 10^{10}$ s$^{-1}$. In the second run, cryo-SAXS data from sub-microliter samples and room temperature SAXS data were acquired with an X-ray energy of 10.0 keV, a sample-detector distance of 1.35 m, a beam size of 220 μm×190 μm (height×width, FWHM), and an X-ray flux of $1.0\times 10^{11}$ s$^{-1}$. The downstream vacuum window was Kapton film rather than $Si_3N_4$.

Background Subtraction.

Conventional SAXS sample cells use parallel, X-ray transparent windows to define a fixed path length. Scattering curves are collected from sample and matching buffer solutions held in identical cells, each is normalized by the transmitted X-ray intensity measured during the exposure, and the two are subtracted to obtain the macromolecule's scattering profile. The cryo-SAXS sample holders described above do not define a fixed path length for the sample, so a normalization and background subtraction method was devised to account for path length variation. The total scattering measured at the detector, $I_{total}(q)$, is modeled as $$I_{total}(q) \propto I_0 T \{\log(1/T)[I_M(q)+I_S(q)]+I_{bkg}(q)\}$$

where $I_0$ is the incident intensity, T is the X-ray transmission factor of the sample (and thus $\log(1/T)$ is proportional to the thickness), $I_M(q)$ and $I_S(q)$ are the scattering from the macromolecule and solvent, respectively, and $I_{bkg}(q)$ is the instrumental background scattering. With appropriate normalization, $I_M(q)$ can be found from three scattering profile measurements: one of the macromolecule-containing sample, one of the macromolecule-free buffer, and one of the empty cell. The incident and transmitted intensities, $I_{incident}$ and $I_{transmitted}$, are measured at the same time as $I_{total}(q)$, and T is calculated using $$T=(I_{incident,empty}/I_{transmitted,empty})\times(I_{transmitted}/I_{incident})$$

where the first factor, obtained from measurements of the empty cell, is included to cross-calibrate the two detectors. A background subtracted, thickness normalized intensity can be computed for both the sample (macromolecule plus buffer) and the buffer. Here background subtraction refers to removing the properly scaled instrumental background scattering:

$$I_\Delta(q) \equiv (I_{total}(q)/I_{transmitted} - I_{total,empty}(q)/I_{transmitted,empty})\times(1/\log(1/T)).$$

Then, the difference between buffer and sample curves $I_{diff}(q)=I_{\Delta,sample}(q)-I_{\Delta,buffer}(q)$ is proportional to $I_M(q)$, the scattering of the macromolecule.

Estimation of X-Ray Dose.

The X-ray dose D delivered to the sample was calculated using $D=t_{exp}fE(1-T)/(V\rho)$, where $t_{exp}$ is the exposure time, f is the X-ray flux (photons per second), E is the X-ray energy, T is the sample transmission factor, V is the illuminated volume, and p is the mass density. The density $\rho\approx 1.07$ g/cm$^{-3}$ was estimated from available data on PEG-water mixtures at room temperature. For each sample, the illuminated volume was found from $V\approx A\mu^{-1}\log(1/T)$ where A is the beam area (product of width and height at FWHM) and $\mu^{-1}$ is the X-ray absorption length. The absorption length was calculated from atomic absorption data and by approximating the 45% (w/w) PEG-200 water mixture as tetra (ethylene glycol) and water in a 1:13 molar ratio (i.e. $H_{44}O_{18}C_8$) with the density given above; at 10 keV, $\mu^{-1}\approx 2.15$ mm. In X-ray crystallography, dose calculations are typically based on the mass-energy absorption coefficient. At the X-ray energies used, this calculation agrees with one based on the mass-energy absorption coefficient to within 1%.

An accurate measure of the beam size at the sample position is required for computing the X-ray dose. X-ray burns in a 1 mm thick glass slide were acquired with exposures of 1, 2, 8, 16, and 32 seconds, digitized using a flatbed scanner at 12,800 dpi (EPSON Perfection 1660), and analyzed in MATLAB. The images were corrected for the nonlinear response of the glass using a calibration curve generated from the multiple exposures.

Analysis of SAXS Profiles.

The pair-distance distribution function P(r) was calculated from the SAXS profiles using the Bayesian Indirect Fourier Transform (BIFT) method. An indirect Fourier transform program with smoothness regularization was written in MATLAB, and Bayesian estimation was used to find the maximum particle dimension $D_{max}$, the Lagrange multiplier a, and the noise level p. In addition, the evidence for the hypothesis was computed (i.e., the probability of the data given the basis set, noise model, and regularizer).

Ab initio reconstructions of the low-resolution particle envelope from SAXS data were performed using the ATSAS suite of programs. For each SAXS curve, 16 DAMMIF reconstructions (fast mode, no symmetry) were aligned and averaged using DAMAVER. Each average reconstruction was aligned with its corresponding atomic structure using SUPCOMB and visualized using Pymol version 1.2rl (DeLano Scientific LLC).

PEG-200 Solutions Yield Good Contrast, Low Background Scattering and Complete Vitrification of 1 µL Drops.

Excessive and irreproducible ice formation on cooling has been a major obstacle to cryo-SAXS. In biomolecular cryocrystallography, the cooling rate and the choice and concentration of cryoprotectant are key variables in obtaining a homogeneous, fully vitrified state at T=100K. Cryo-SAXS imposes additional constraints. Most cryoprotectants have higher electron densities than water. Adding cryoprotectant thereby increases the solvent's average electron density and its electron density fluctuations, decreasing SAXS contrast and increasing solvent background scattering. Consequently, cryoprotectants that are effective at low concentrations and that have electron densities near that of water are preferred. Based upon these criteria, we find PEG-200 to be the superior choice among several other small-molecule cryoprotectants tested (including glycerol, ethylene glycol, and DMSO).

The cryoprotectant concentration necessary for complete vitrification was determined by acquiring cryo-SAXS profiles (FIGS. 10(c), (d) and (e)) at several PEG-200 concentrations from ~1 microliter PEG-water drops cooled to 100 K in a $N_2$ gas stream. FIG. 10(a) shows photographs of the drops held in ~700 µm nylon loops after cooling. PEG concentrations for drops (A-H) ranged from 0% to 45% (w/w). Opacity of the drop arises from light scattering by ice crystals.

In the SAXS data (FIG. 10(b), (c)), at concentrations below 45% (w/w), the presence of ice is indicated by a steep rise in the scattered intensity below q≈0.02 Å$^{-1}$, in some cases to almost four orders of magnitude above the profile's high-q baseline. When plotted on a log-log scale (FIG. 10(d)), it can be seen that the signature of ice formation is a power law at all concentrations.

The SAXS curves in FIGS. 10(b) and (c) show increasing scattering intensity at q≲0.02 Å$^{-1}$ as the PEG concentration increases from 0 to 35% (w/w). At 40% (w/w) PEG and above the drops are visually clear and the q≲0.02 Å$^{-1}$ intensity drops dramatically. However, scattering at low q values still shows the presence of small amounts of ice. At 45% (w/w) PEG, the low-q scattering is 10 times the baseline level in one sample (G), and absent in a second sample (H). In photographs of the sample drops (FIG. 10(a)), samples F and G, with PEG concentrations of 40% and 45% (w/w), respectively, are both visually clear. Thus, sample clarity is not a sufficient indicator of complete vitrification in the context of cryo-SAXS.

At PEG concentrations above 45% (w/w), no ice signal was observed, and samples could be reliably vitrified. Similar measurements yielded minimum concentrations for ice-free cryo-SAXS profiles of 50% (w/w) for glycerol, 50% (w/w) for ethylene glycol, and 45% (w/w) for DMSO. These cryoprotectant concentrations are roughly 5% larger than are required to eliminate ice rings in crystallographic diffraction at comparable cooling rates.

Sample Cell Design and Buffer Subtraction Technique Enable Collection of Cryo-SAXS Data from Biomolecules.

The window-free, thin-wall sample cell in FIG. 9(b) was designed to optimize the X-ray path length through the 1 microliter sample for good signal to noise, and to maximize heat transfer rates through its sidewalls for rapid cooling. The X-ray beam passed along the axis of the cylindrical cell, and the sample was held within it by surface tension prior to cooling. At the Cornell High Energy Synchrotron Source (CHESS), a cryostream cooler was incorporated into the G1 beamline's SAXS setup, allowing sample cooling by a continuous nitrogen gas stream at a temperature of 100 K.

In conventional SAXS on liquid samples, the fixed sample cell windows precisely define the X-ray path length, allowing buffer subtraction of data acquired in the same cell. In our window-free cell, the path length depends on the sample's volume and the shape of its meniscus. A three-curve background subtraction method was used to correct for inevitable path length variations, as described above. To demonstrate this method, FIG. 9(c) shows cryo-SAXS profiles for a 2 mg/mL glucose isomerase (GI) solution and its matching buffer, as well as the instrumental background. Each solution contained the cryoprotectant PEG-200 at 45% (w/w) concentration. Slight differences in the X-ray path lengths through the GI and buffer samples contributed to differences in their scattering. In FIG. 9(d), subtraction of the normalized and background subtracted GI and buffer solution profiles reveals the small oscillations at high-q that are characteristic of a large, sphere-like globular protein.

Radius of Gyration, Maximum Dimension, and Particle Envelope Determined by Cryo-SAXS for Glucose Isomerase.

Figure 11:
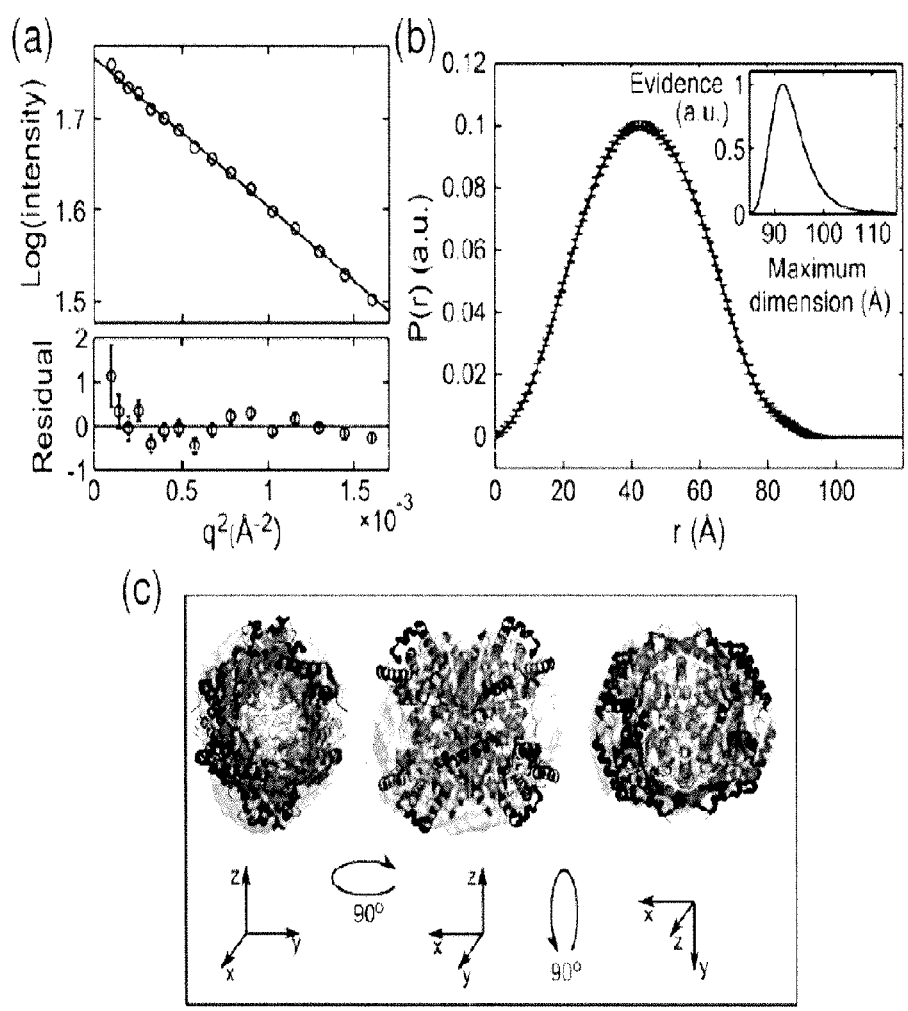
FIG. 11. (a) Guinier plot of cryo-SAXS data from glucose isomerase with linear fit used to find the radius of gyration $R_g$. (b) The pair distance distribution function P(r) derived from the Fourier transform of the scattering profile, and deduced maximum particle dimension (inset). (c) Three orientations of the reconstructed particle envelope with the docked crystal structure.

Macromolecular SAXS data are most often used to find shape information, including the radius of gyration ($R_g$), the maximum particle dimension, and the low resolution envelope. To assess whether cryo-SAXS data are of sufficient quality for these purposes, the cryo-SAXS profile for 2 mg/ml GI was analyzed using standard techniques. The Guinier plot in FIG. 11(a) is linear within the noise down to the smallest angles measured (q=0.01 Å$^{-1}$), and the slope gives a radius of gyration $R_g$=33.4±0.1 Å in excellent agreement with the crystal structure-derived value of 33.35 Å (CRYSOL with default parameters and PDB 1XIB). The pair-distance distribution function P(r) in FIG. 11(b) has a Gaussian shape characteristic of a globular particle, and gives a well-defined maximum dimension. An ab initio reconstruction of the molecular envelope without symmetry constraints shows fair agreement with the tetrameric structure from MX. In FIG. 11(c), the mean NSD between the reconstructed particle envelope and the docked crystal structure is 0.641. Imposing appropriate symmetry constraints during reconstruction improves the agreement.

Figure 12:
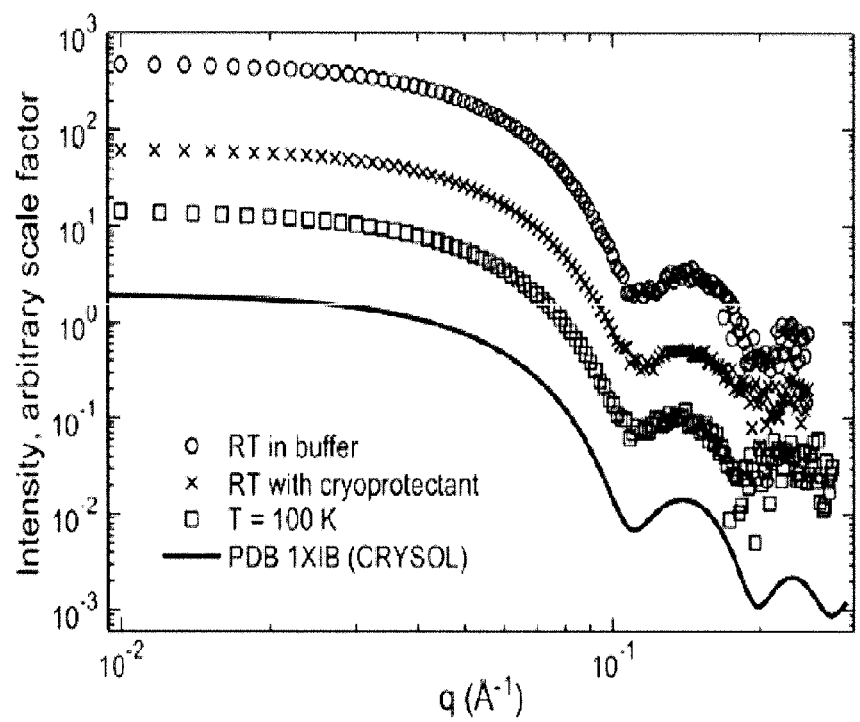
FIG. 12. Background subtracted and normalized SAXS profiles from 2 mg/ml glucose isomerase at room temperature and 100 K.

To determine whether the cryoprotectant or the cooling process significantly alters the SAXS profile, data were collected at room temperature (RT) from GI in buffer with and without 45% (w/w) PEG-200 cryoprotectant. The samples were oscillated through the beam within a stationary quartz capillary to reduce radiation damage. As shown in FIG. 12, The most obvious effect of PEG-200 is a reduction in signal intensity due to lower electron density contrast between protein and solvent. Assuming average electron densities of 0.334 Å$^{-3}$ for water, 0.420 Å$^{-3}$ for protein, and 0.355 Å$^{-3}$ for a 45% (w/w) PEG-200 water solution at 298 K, the scattering of protein in 45% (w/w) PEG should be 57% of its scattering in pure water. This is consistent with the observed two-fold reduction in scattering intensity of GI in PEG compared with standard buffer at room temperature. Despite this change in intensity, the overall shape of the scattering curve for GI is otherwise unchanged (FIG. 12). Rg determined from the Guinier plot was 32.8±0.1 Å in buffer and 32.5±0.1 Å with cryoprotectant added. These values agree within experimental error with the average $R_g$ of 32.7±0.2 Å determined in previous SAXS studies of GI.

FIG. 12 shows that the presence of cryoprotectant (45% w/w PEG-200) and rapid cooling to 100 K do not affect the essential features of glucose isomerase's scattering profile, as determined at room temperature in cryoprotectant-free buffer. The profile's shape and calculated $R_g$ are similar to those from room temperature measurements and from the crystal structure prediction. The CRYSOL prediction from the crystal structure of GI was calculated using default parameters, and is shown for reference. For display purposes, the curves in FIG. 12 were multiplied by an arbitrary scale factor. The total exposure times for room temperature samples were 32 s in aqueous buffer and 52 s in PEG buffer. The sample at T=100K was exposed for 180 s (corresponding to a dose of 220 kGy).

Small differences between the 100 K and room temperature SAXS curves are observed in the Guinier region. The calculated $R_g$ is ~2% larger at 100 K. This difference is small compared with experimental uncertainties, and may arise from differences in the sample geometry for 100 K and room temperature measurements, and also from residual interparticle interference at the working concentration of 2 mg/ml. However, since a protein's SAXS profile includes scattering from a hydration layer of ordered water molecules, the 2% increase in $R_g$ at 100K may reflect increased hydration water ordering, as is seen in protein crystals.

SAXS from Cryocooled Glucose Isomerase is Insensitive to Large X-Ray Doses.

X-ray induced changes to the macromolecule's structure or solution state must be minimized to obtain reliable SAXS profiles. In room temperature solution SAXS, a series of profiles are acquired and inspected for dose and time-dependent changes using the radius of gyration as a means of quantifying damage and determining the maximum tolerable X-ray exposure. Collecting data on vitrified samples at T~100 K should eliminate radiation induced aggregation (which otherwise dominates low-angle scattering) and reduce unfolding and fragmentation.

Figure 13:
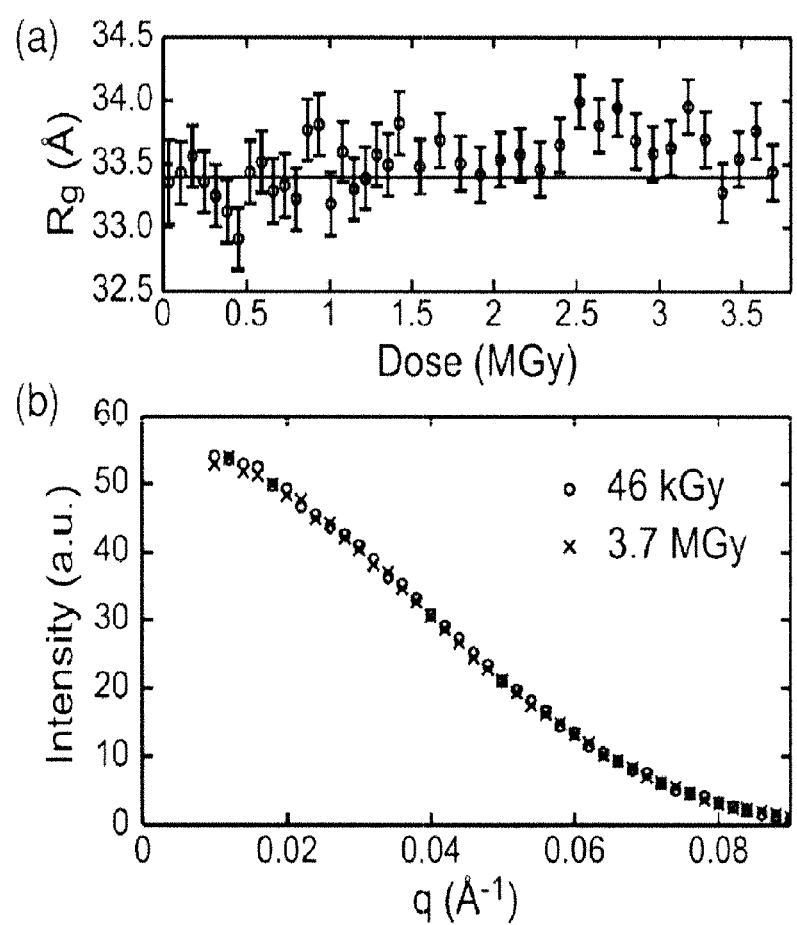
FIG. 13. (a) Radius of gyration ($R_g$) of GI as a function of accumulated X-ray dose for a single sample shows no radiation damage even at high doses. $R_g$ was calculated from the region 0.02<q<0.04 Å$^{-1}$, and standard errors computed from the fits are shown. (b) The first and last SAXS profiles in the dose series of (a) are indistinguishable.

To verify that data collection at T=100K reduces the rate at which radiation damage is manifested in SAXS profiles, a series of 60 s exposures were acquired from a ~1 microliter GI+buffer sample and then from a buffer-only sample. The accumulated dose for each exposure was calculated from the incident X-ray beam intensity and illuminated volume as described above. GI's SAXS profile at a given dose was obtained by subtracting a buffer curve at roughly the same dose. FIG. 13(a) shows that at all doses, the $R_g$ values fall between 33 and 34 Å and do not show any obvious dose-dependence. FIG. 13(b) shows that the SAXS profiles obtained from the first and last exposures (corresponding to the smallest and largest dose in FIG. 13(a) are indistinguishable. The final exposure corresponds to an accumulated dose of 3.7 MGy.

In cryoelectron microscopy and diffraction, in X-ray cryocrystallography, and in X-ray diffractive imaging of biological samples, all proteins show similar radiation sensitivity—measured on a damage per dose basis—at T=100K, and this should also be true in cryo-SAXS. For these other diffraction techniques, the maximum tolerable dose at T=100K to achieve a data set of a given resolution (in A) is roughly 10 MGy/A. For a SAXS data set to q=0.3 Å$^{-1}$, corresponding to a resolution of ~20 Å, this yields a maximum tolerable dose of 200 MGy. However, analysis of SAXS data is sensitive both to loss of information at high-q and to radiation-induced changes at low-q. At room temperature, radiation damage first manifests at low-q, presumably because of molecular aggregation, fragmentation and unfolding, processes that should be strongly suppressed at T=100K. However, at large doses, microscopic inhomogeneities due to, for example, radiolytic cleavage of hydrogen and subsequent recombination and diffusion, may develop. In cryoelectron microscopy, hydrogen bubbles become evident beyond doses of ~1000-10,000 electrons/nm$^2$ corresponding to doses of ~45 MGy. Recent SAXS measurements on cryo-cooled insulin crystals observed a strong increase in scatter attributed to hydrogen bubble formation beyond ~70 MGy, increasing to >180 MGy for T≤30 K. Consequently, for typically radiation sensitive biomolecules with room temperature dose limits of 1-10 kGy, cryo-SAXS should yield dose limit increases of between two and five orders of magnitude, and corresponding reductions in minimum sample volumes.

High Dose Tolerance Enables Macromolecular Envelope Reconstruction from Nanoliter Sample Volumes.

Because of the greatly increased dose tolerance at T=100K, cryo-SAXS should enable dramatic reductions in minimum sample volumes for macromolecular envelope reconstruction. To demonstrate this, cryo-SAXS data were collected from non-spherical drops with thicknesses between 300 and 500 µm, held within polyimide crystallography loops with a 600 µm diameter a shown in FIG. 14(a). The X-ray illuminated volume (the product of the drop thickness and beam area) ranged from 13 to 25 nL.

With this non-ideal sample geometry, accurate buffer subtraction at high-q was more difficult to achieve than with the sample holders of FIG. 9(b). In general, SAXS patterns from macromolecules decay rapidly toward background at high q. This makes the high-q background subtraction exquisitely sensitive to errors in the normalization of sample and buffer curves. Although we were unable to identify sources of these errors, SAXS profiles of multiple cryo-cooled drops containing the same PEG-buffer solution have subtraction errors that are well approximated within noise by a constant offset.

To correct for these background subtraction errors in sub-microliter drops, constant offsets were chosen to maximize the so-called Bayesian evidence of the P(r) function obtained using the Bayesian Indirect Fourier Transform (BIFT) method. The implementation of BIFT is described above, and we have demonstrated its ability to correct offset errors under experimental conditions is demonstrated with synthetic data. In general it is not good practice to add offsets to SAXS profiles, as the high-q scattering is used to determine the foldedness (Kratky plot) and volume (Porod invariant) of the macromolecule. However, this correction can be done without biasing envelope reconstructions. For example, the program DAMMIN/F of the ATSAS suite by default adjusts the constant offset to account for the bead model's inability to accurately represent internal density fluctuations.

Figure 14:
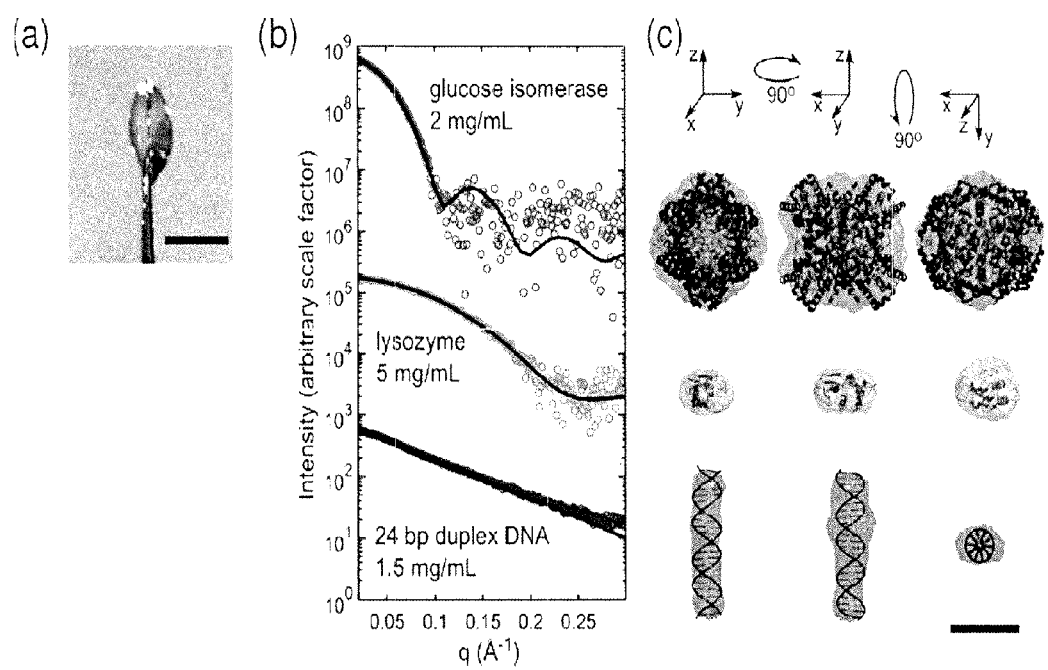
FIG. 14. (a) Small, lenticular sample drops were held in a 600 μm diameter polyimide crystallography mount. The scale bar in the image is 500 μm. (b) Cryo-SAXS data acquired for glucose isomerase (GI), hen egg white lysozyme, and 24 base-pair duplex DNA at the indicated concentrations. (c) Macromolecule envelopes generated from the cryo-SAXS data were aligned with the atomic structures, and are shown in three orientations. All are scaled according the 50 Å bar at lower right.

FIG. 14(b) shows cryo-SAXS profiles for GI, lysozyme, and 24-bp DNA duplex. Each profile was determined from one sample drop and one buffer drop, with an X-ray dose to the nanoliter samples of between 100 and 300 kGy. Solid lines in (b) show the CRYSOL predictions from each atomic structure, based on PDBs 1XIB and 2LYZ, and an ideal 24-bp DNA helix generated using Nucleic Acid Builder. No fitting parameters were used except for an overall scale factor for the (arbitrary) intensity. For GI, lysozyme and DNA, the X-ray illuminated sample volumes were 16.3, 13.6 and 24.9 nL; the exposure times were 160, 80, and 160 seconds; the X-ray doses were 275, 114, and 234 kGy; and the mean NSDs were 0.586, 0.459 and 0.542, respectively. Although the SAXS profiles are noisy, as shown in FIG. 14(c), in all cases the profiles are sufficient to obtain molecular envelopes in reasonable agreement with atomic structures determined from crystallography.

The results presented here demonstrate the basic feasibility of cryo-SAXS as a method for determining structural information from macromolecules in sub-microliter volume samples. Macromolecular solutions can be cooled into a vitrified state exhibiting no excess low-q scatter, indicating the absence of ice or other inhomogeneities on the length scales probed by SAXS. Required cryoprotectant concentrations are tolerable, produce modest reductions in SAXS contrast, and (at least for the macromolecules studied here) do not affect macromolecule structure. Because aggregation, unfolding, fragmentation and other degradation processes that generate sample inhomogeneities are largely eliminated in vitrified samples, radiation damage per unit dose is reduced by at least two and as much as five orders of magnitude relative to room-temperature SAXS; unless radiation-induced hydrogen bubble formation becomes important, cryo-SAXS dose limits should be ~100 MGy, substantially larger than in cryocrystallography because of the lower resolution provided by SAXS. This large decrease in radiation sensitivity allows minimum sample volumes to be reduced by a comparable factor. Solvent and instrumental background subtraction is possible even with non-ideal and non-identical macromolecule and buffer sample geometries, allowing determination of radii of gyration and structural envelopes that match results from crystallography.

While elimination of ice crystallites allowed us to subtract cryo-SAXS buffer scattering at low-q, reliable buffer subtraction at high-q is still a challenge. Sample geometry nonidealities and irreproducibilities and drift in instrumental background introduce errors. However, by configuring the SAXS beamline to minimize background, designing a sample cell to optimize signal to noise, and measuring and correcting for path length variations, we were able to demonstrate reasonable buffer subtraction for 2 mg/ml GI.

The primary effect of the 45% (w/w) PEG-200 concentration used here was a ~two-fold reduction in macromolecule contrast. However, cryoprotectants may also have effects on macromolecular structure and interactions. Cryoprotectants are osmolytes, and therefore modify water activity and macromolecule hydration. High osmolyte concentrations have been used to mimic cellular conditions in vitro, and therefore may help preserve biologically relevant solution structures over some concentration range. Glycerol is known to stabilize protein structure and prevent aggregation. PEG-200 decreases the melting temperature of nucleic acid secondary structures, but stabilizes tertiary structures. These and other effects of cryoprotectant will have to be taken into account when comparing cryo-SAXS results with those from other techniques. Smaller sample volumes and the use of liquid nitrogen or propane instead of gaseous nitrogen as the cooling agent should allow cryoprotectant concentrations to be decreased below 30%, comparable to values routinely used in cryocrystallography and generally assumed to have negligible effects on macromolecule structure.

The use of cryocooling has the potential to eliminate many difficulties associated with room temperature SAXS experiments. Because vitrified samples are much more radiation tolerant, they may yield much larger integrated signal to noise with no concerns about damage. Samples that spontaneously aggregate or otherwise degrade with time can be frozen immediately after manufacture and stored indefinitely, eliminating concerns about long-term stability. Dramatically reduced sample volume requirements will facilitate mass screening of solution conditions for their effects on molecular structure or association, and combinatorial binding assays to, e.g., elucidate pathways for macromolecular complex formation. Short turnaround times will result from exploiting the existing infrastructure for high-throughput crystallography, including mail-in facilities that employ automated sample handling and full brightness, for rapid turn-around data collection. In the same way that cryo-MX has transformed atomic resolution studies, cryo-SAXS is poised to transform low-resolution studies of macromolecular structure and function.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

We claim:

1. A cryogenic, small angle X-ray scattering (SAXS) application sample holder, comprising:
   a sample cell including a base portion and at least two parallel walls disposed on the base,
   wherein the sample cell has a liquid volume capacity defined by the walls and the base portion of 0.001 to 10 microliters, and wherein each of the base portion and the at least two parallel walls are structured and configured to directly contact a liquid sample when in use.

2. The sample holder of claim 1, wherein the at least two parallel walls consist of two walls that are offset.

3. The sample holder of claim 1, further comprising a sample cell support structure to which the sample cell can be coupled, whereby the support structure is adapted to hold and position the sample cell in an X-ray beam, wherein the sample cell and coupled support structure have known physical characteristics allowing the sample to be cooled at a rate of at least 100 K/s.

4. The sample holder of claim 1, where the base portion and the walls are one or more of a polymer, silicon, silicon nitride, silicon dioxide, graphene.

5. The sample cell of claim 1 or 3, wherein the walls have a thickness of between 0.001 and 100 microns.

6. The sample cell of claim 5, where the at least two parallel walls have a thickness of between 0.1 and 50 microns.

7. The sample cell of claim 1 or 3, wherein the at least two parallel walls have a separation distance of between 0.1 mm and 5 mm.

8. The sample cell of claim 7, wherein the at least two parallel walls have a separation distance of between 0.5 mm and 2 mm.

9. The sample cell of claim 1 or 3, wherein the at least two parallel walls have a height and a width of between 10 and 1000 microns.

10. The sample cell of claim 9, wherein the at least two parallel walls have a height and a width of between 100 and 500 microns.

11. The sample cell of claim 1 or 3, wherein the at least two parallel walls have a maximum surface roughness of less than 10 nm.

12. The sample cell of claim 1 or 3, further comprising a contact line pinning ridge disposed along a vertical end of each of the at least two parallel walls.

13. The sample cell of claim 1 or 3, further comprising one or more side walls connected in a transverse orientation to a respective one of the at least two parallel walls.

14. The sample cell of claim 13, wherein the one or more side walls extend beyond the ends of the at least two parallel walls.

15. The sample cell of claim 13, wherein the one or more side walls are connected to the respective ends of two of the at least two parallel walls, further wherein the one or more side walls have an aperture, whereby a liquid can be injected there through and which allow a sample to expand or contract as it is cooled to cryogenic temperature and then warmed to a higher temperature.

16. The sample cell of claim 1 or 3, further comprising a support attached to an exterior face of at least one of the at least two parallel walls, whereby to support the walls and prevent their deflection or damage due to forces exerted by a sample between the walls as the sample is cooled to cryogenic temperatures and warmed.

17. The sample cell of claim 1 or 3, further comprising a plurality of sample cells having a common base portion.

\* \* \* \* \*